United States Patent
Morales et al.

(10) Patent No.: US 10,174,032 B2
(45) Date of Patent: Jan. 8, 2019

(54) HETEROCYCLIC COMPOUND CLASSES FOR SIGNALING MODULATION

(71) Applicant: SignalRx Pharmaceuticals, Inc., San Diego, CA (US)

(72) Inventors: Guillermo A Morales, Oro Valley, AZ (US); Joseph R. Garlich, Volcano, HI (US); Kevin T. Weber, Carmel, IN (US); Jessica M. Newblom, Indianapolis, IN (US); Donald L. Durden, San Diego, CA (US)

(73) Assignee: SignalRx Pharmaceuticals, Inc., San Diego, CA (US)

( * ) Notice: Subject to any disclaimer, the term of this patent is extended or adjusted under 35 U.S.C. 154(b) by 27 days.

(21) Appl. No.: 14/702,816

(22) Filed: May 4, 2015

(65) Prior Publication Data
US 2015/0315207 A1    Nov. 5, 2015

Related U.S. Application Data

(60) Provisional application No. 61/988,346, filed on May 5, 2014.

(51) Int. Cl.
| | |
|---|---|
| C07D 498/04 | (2006.01) |
| C07D 495/04 | (2006.01) |
| C07D 487/04 | (2006.01) |
| C07D 473/18 | (2006.01) |

(52) U.S. Cl.
CPC ......... *C07D 473/18* (2013.01); *C07D 487/04* (2013.01); *C07D 495/04* (2013.01); *C07D 498/04* (2013.01)

(58) Field of Classification Search
CPC .. C07D 495/04; C07D 498/04; C07D 487/04; C07D 473/18
See application file for complete search history.

(56) References Cited

U.S. PATENT DOCUMENTS

| | | | | |
|---|---|---|---|---|
| 3,475,429 | A  * | 10/1969 | Woitun | C07D 495/04 514/822 |
| 8,557,807 | B2 | 10/2013 | Morales et al. | |
| 9,492,455 | B1 * | 11/2016 | Seyfang | A61K 31/12 |
| 2013/0029969 | A1* | 1/2013 | Homma | C07D 495/04 514/210.21 |

OTHER PUBLICATIONS

Kikta et al. Organic Magnetic Resonance, 1976, vol. 8, Iss. 4, pp. 192-197.*
Tan et al. J. Comb. Chem., 2007, vol. 9, pp. 210-218.*
Radi et al. J. Med. Chem., 2011, vol. 54 pp. 2610-2626.*
Tominaga et al. Yakugaku., 1979, vol. 99, pp. 1081-1090.*
Gutorov et al. Patent SU 653260, 1979, English Abstract.*
U.S. Appl. No. 14/041,279, filed Mar. 13, 2014, Guillermo Morales et al.
U.S. Appl. No. 14/702,822, filed May 4, 2015, Donald Durden et al.

* cited by examiner

*Primary Examiner* — Samira J Jean-Louis
(74) *Attorney, Agent, or Firm* — TDW Patents & Consulting; Thomas D. Webster

(57) ABSTRACT

The invention relates to compounds of Formulas I-VII (or pharmaceutically acceptable salts thereof) as defined herein, pharmaceutical compositions thereof, and their use in manufactures and methods for modulating cellular signaling pathways and biological processes associated therewith including inhibition of kinase activity such as PI-3 kinase or inhibition of bromodomain proteins or both at the same time as well as to therapeutic methods for treating a disease associated with aberrant PI3K and/or bromodomain proteins.

2 Claims, 1 Drawing Sheet

HETEROCYCLIC COMPOUND CLASSES FOR SIGNALING MODULATION

CROSS REFERENCE TO RELATED APPLICATIONS

This application claims the benefit of U.S. Provisional Application No. 61/988,346 filed May 5, 2014, herein incorporated by reference.

FIELD OF THE INVENTION

The present invention relates to new heterocyclic compounds that demonstrate activity as cell signaling and/or epigenetic modulators including inhibitors of kinases or bromodomain proteins or both, and methods of using the compounds in therapeutic applications including but not limned to as anti-tumor agents in mammals.

BACKGROUND

Cell signaling is widely recognized as a key component in normal cell proliferation and cell death, and in neoplastic transformation. A number of distinct biochemical pathways have been identified within this genre. One of these, the PI-3 kinase (PI-3K or PI3K) pathway (also known as the PI-3 Kinase/AKT pathway), is involved in the production of the second messenger molecule PtdIns(3,4,5)P3 (PIP$_3$). Molecular and genetic studies have shown a strong correlation between the PI-3 kinase pathway and a variety of diseases in humans such as inflammation, autoimmune conditions, and cancers. (See P. Workman et al., *Nat. Biotechnol.* 2006, 24, 794-796; I. Vivanco et al., *Nat. Rev. Cancer* 2002, 2, 489-501). The PI-3 kinase pathway controls a number of cellular functions including cell growth, metabolism, differentiation, and apoptosis. Many types of cancer are thought to arise in response to abnormalities in signal transduction pathways such as the PI-3 kinase pathway. The PI-3 kinase pathway comprises a number of enzymes including PI-3 kinase, PTEN (Phosphatase and Tensin homolog deleted on chromosome Ten), and AKT (a serine/threonine kinase also known as PKB) all of which are involved in producing and maintaining intracellular levels of the second messenger molecule PtdIns(3,4,5)P3 (PIP$_3$). Homeostasis of this important second messenger is maintained by PI-3 kinase and PTEN. When either PI-3 kinase or PTEN are mutated and/or reduced in activity, PIP$_3$ levels are perturbed and this perturbation may act as a trigger in the development of cancer. Indeed, both PI-3 kinase and PTEN have been found to be mutated in multiple cancers including glioblastoma, ovarian, breast, endometrial, hepatic, melanoma, gut, lung, renal cell, thyroid and lymphoid cancer. The Class IA isoform of the regulatory subunit of PI-3 kinase, p110α, is frequently over-expressed and mutated in many cancers including gliomas, colon, brain, breast, lung, prostate, gynecological and other tumor types (Ibid.; Y. Samuels et al., *Science*, 304, 554 (2004)). Thus, a rational approach in treating cancer relates to developing drugs that act on signaling pathways including the kinases of the PI-3 kinase pathway.

The PI-3 kinase family comprises roughly 16 members divided into 3 classes based on sequence homology and the particular product formed by enzyme catalysis. Class I PI-3 kinases have 2 subunits: a 110 kd catalytic subunit and an 85 kd regulatory subunit. Class I PI-3 kinases are involved in important signal transduction events downstream of cytokines, integrins, growth factors and immunoreceptors. Inhibition of class I PI-3 kinase induces apoptosis, blocks tumor-induced angiogenesis in vivo, and increases radiosensitivity in certain tumors.

Other mechanisms for cancer involving loss of a negative regulator have also been identified. For example, PTEN, a lipid phosphatase, regulates signaling through the PI-3 kinase pathway by dephosphorylating PIP3, the product of PI-3 kinase (for review see L. C. Cantley et al., *Proc. Natl. Acad. Sci.* 1999, 96, 4240-4245). Tumors having mutations in the PTEN tumor suppressor gene have been identified in a number of different cancers. As a consequence of PTEN loss and the resultant increase in PIP3 levels, signal propagation through downstream kinases such as AKT is constitutively elevated. Preclinical studies suggest that this constitutive kinase activation creates a kinase dependency analogous to that in tumors with activating mutations in the kinase itself.

Genetic and biochemical evidence has shown that constitutive activation of AKT can regulate TOR (mTOR in mammalian systems) through phosphorylation of the tuberous sclerosis complex (K. Inoki et al., *Nat. Cell Biol.* 2002, 4, 648-657). Hence, tumors with loss-of-function mutations in PTEN exhibit constitutive activation of AKT, as well as other downstream kinases such as mTOR, and many tumors in murine models are sensitive to mTOR inhibitors (M. S. Neshat et al., *Proc. Natl. Acad. Sci.* 2001, 98, 10314-10319).

Therapeutic agents that target key signaling pathways are of considerate interest, LY294002 (2-(4-morpholinyl)-8-phenyl-4H-1-benzopyran-4-one) is a first-generation potent, non-selective inhibitor of PI-3 kinases with an IC50 of 1.4 μM (C. J. Vlahos et al., *J. Biol. Chem.* 1994, 269, 5241-5248). While LY294002 is an effective inhibitor of PI-3 kinase, and has found utility as a pharmacological tool, it has several undesirable attributes that render it unsuitable for clinical use, including lack of aqueous solubility, poor pharmacokinetics, unacceptable toxicity, lack of tissue specificity, rapid metabolism in animals, and a synthetic route that uses carbon disulfide, a highly toxic compound. As such, LY294002 has never been developed for clinical use but has stimulated the search for improved PI-3K inhibitors of which over 10 are in clinical development and one has received FDA approval.

Tumorigenesis, as well as other disease conditions, may also result from epigenetic-induced changes in gene expression and cellular phenotype in the absence of nucleic acid mutations. Epigenetic effects have been attributed to acetylation of lysine residues on proteins. Three types of proteins appear to be important in this process: the "writers" (i.e., DNA methyltransferase which adds methyl groups to DNA), the "erasers" (i.e., histone deacetylase, HDAC, which removes acetyl groups from histones), and the "readers" (i.e., BET bromodomain proteins, such as BRD2, BRD3, BRD4 and BRDT in humans). A number of bromodomain proteins have been identified and correlated with various diseases. See e.g. Muller et al., *Expert Reviews in Molec. Med.* 13, 1-21, 2011 herein incorporated by reference. The bromodomain proteins serve as "readers" for chromatin to recruit regulatory enzymes such as the writers and erasers of histone modification which can then lead to regulation of gene expression.

Inhibitors of BET proteins are potentially useful in the treatment of a number of conditions including but not limited to obesity, inflammation, and cancer (A. C. Belkina et al., Nat. Rev. Cancer 2012, 12, 465-477). BET inhibitors act as acetylated lysine mimetics which disrupt the binding interaction of BET proteins with acetylated lysine residues on histones (D. S. Hewings et al., J. Med. Chem. 2012, 55, 9393-9413). This disruption leads to suppression of transcription of genes involved in cancer including c-MYC, MYCN, BCL-2, and some NF-kB-dependent genes (J. E. Delmore et al., Cell 2011, 146, 904-917; A. Puissant, Cancer Discov. 2013, 3, 308-323). For example, B-cell malignancies are associated with the activation of the c-MYC gene which is partially controlled by the PI-3 kinase-AKT-GSK3beta signaling axis (J. E. Delmore et al., Cell 2011, 146, 904-917). MYC (encompassing c-MYC and MYCN) is an oncoprotein that has been difficult to inhibit using small molecule approaches (E. V. Prochownik et al., Genes Cancer 2010, 1, 650-659).

Recently it has been shown that BET inhibition prevents the transcription of MYCN (A. Puissant, Cancer Discov. 2013, 3, 308-323), and blocking PI-3K enhances MYC degradation (L. Chester et al., Cancer Res. 2006, 66, 8139-8146). Therefore, a single molecule that inhibits both PI-3K and bromodomain proteins would provide a novel and potentially more effective way to inhibit MYC activity.

Several recent reviews cover the inception and status of the bromodomain inhibitor field including D. Gallenkamp et al., Chem. Med. Chem., 2014, 9, 438-464 and S. Muller et al., Med. Chem. Commun. 2014, 5, 288-296. Most recently it has been reported that inhibition of BET bromodomain proteins such as BRD4 can prevent the kinome adaptation response (i.e., induced transcriptional upregulation of multiple kinases involved in resistance mechanisms) found for tyrosine kinase inhibitor drugs, such as lapatinib (T. J. Stuhlmiller et al., Cell Reports 2015, 11, 390-404).

The need for more efficacious treatments for cancer and other conditions has lead to combination therapies using multiple anticancer agents, or alternatively multitargeting agents in which a single drug blocks more than one target (See D. Melisi et al., Curr. Opin. Pharm., 2013, 13, 536-542).

It is known that some kinase inhibitors also inhibit bromodomain proteins. For example, LY294002 has been shown to inhibit BET bromodomains (A. Dittmann et al., ACS Chem. Biol., 2014, 9, 495-502) with an $IC_{50}$ of 12.43 µM on the BRD4 bromodomain protein (binding region 1). Replacing the morpholine group of LY294002 with a piperizine group (LY303511) causes LY294002 to lose all PI3K inhibition activity and, likewise, replacement with a thiomorpholine group causes LY294002 to lose most PI3K inhibition activity (C. Vlahos et al., J. Biol. Chem. 1994, 269, 5241-5248). However, the piperizine replacement compound (LY303511) has been shown to maintain BRD4 inhibition as it exhibits an $IC_{50}$ of 9.05 µM on the BRD4 bromodomain protein binding region 1 (A. Dittmann et al., ASC Chem. Biol. 2014, 9, 495-502). Other kinase inhibitors have also been found to inhibit BET bromodomains. For example, the PLK1 inhibitor BI2536 and the JAK2 inhibitor TG101209 potently inhibit BET protein BRD4-1 (S W J Ember, ACS Chem Biol., 2014, 9, 1160-1171).

There remains a need for potent inhibitors of PI3K and for potent inhibitors of bromodomain proteins; especially there remains a need for small molecules that inhibit both PI3K and bromodomain proteins such as BRD4. The novel heterocycles of the present invention meet this need by providing compounds with enhanced therapeutic properties useful for inhibiting tumor growth, cancer treatment and other diseases related to aberrant PI3K and/or bromodomain proteins.

SUMMARY OF THE INVENTION

The present invention relates to novel heterocyclic compounds, conjugates thereof, and pharmaceutical compositions for use as cell signaling pathway modulators, including modulators of the PI-3 kinase pathway, and for inhibiting bromodomain proteins from binding their substrates, especially acetylated lysines of chromatin. The invention further relates to use of the compounds, conjugates, and pharmaceutical compositions of the invention as therapeutic agents for inhibiting tumor growth, for the treatment of neoplastic disorders including cancer, and for treating other diseases or conditions that are related to aberrant PI3K and/or bromodomain protein activity.

In one aspect, the present invention relates to a compound of Formula I or a pharmaceutically acceptable salt thereof:

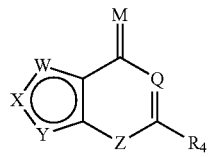

Formula I

Wherein Z is O or NR3;

Q is N;

M is O or S;

W is N, S, or CR1

X is N or CR1;

Y is NR2 or CR3;

R1, R2, R3, and R4 are each independently selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, and boronic ester, azo, substituted azo, azido, nitroso, imino, substituted imino, oxime, substituted oxime, alkoxy, substituted alkoxy, aryloxy, substituted aryloxy, thioether, substituted thioether, carbamate, or substituted carbamate.

In one aspect, the present invention relates to compounds of Formula II-IV or a pharmaceutically acceptable salt thereof:

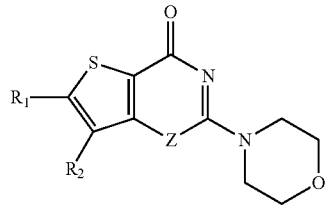

Formula II $Z = O, NR_3$

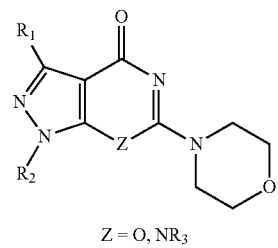

Formula III

Z = O, NR₃

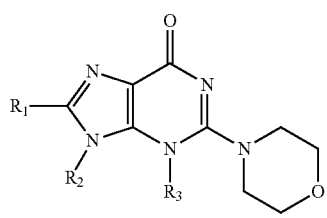

Formula IV wherein R1, R2, and R3 are each independently selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphoric acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, and boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

Alternatively, Formulas II-IV wherein R1, R2, and R3 are selected from any subset of 2, 3, 4, 5, 6, 7, or 8 of substituents selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, and boronic ester, azo, substituted azo, azido, nitroso, imino, substituted imino, oxime substituted oxime, alkoxy, substituted alkoxy, aryloxy, substituted aryloxy, thioether, substituted thioether, carbamate, substituted carbamate.

In another aspect, the present invention relates to compounds of Formula V-VII or a pharmaceutically acceptable salt thereof:

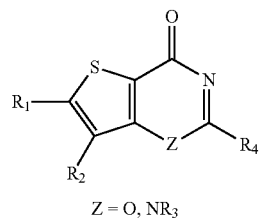

Formula V

Z = O, NR₃

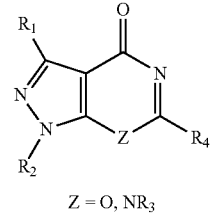

Formula VI

Z = O, NR₃

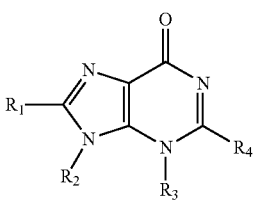

Formula VII wherein R1, R2, R3, and R4 are each independently selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, and boronic ester, azo, substituted azo, azido, nitroso, imino, substituted imino, oxime, substituted oxime, alkoxy, substituted alkoxy, aryloxy, substituted aryloxy, thioether, substituted thioether, carbamate, or substituted carbamate.

Alternatively, Formulas V-VII wherein R1, R2 and R3 are selected from any subset of 2, 3, 4, 5, 6, 7, or 8 is of the substituents selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, and boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate.

As used herein, the expression "a compound of Formula X" (e.g. Formula I, II, III, IV, V, VI, VII, etc.), or the expression "a compound of the invention" includes the compound, conjugates thereof, tautomers thereof, metabolites thereof, and any conventional prodrug thereof, as well as a pharmaceutically acceptable salt of said compound, conjugate, or prodrug. The compounds of the present invention also encompass polymorphic forms, solvates, hydrates, salts and complexes thereof.

Compounds of the invention are useful as cell signaling modulators including inhibiting kinases, for example, mTOR kinase, PIM-1 kinase, PLK-1 kinase, DNA-PK kinase, and Class IA and IB PI-3 kinases and BET bromodomain proteins such as BRD4. Various compounds of Formulas I-VII are useful inhibitors of tumor growth and for the treatment of cancer and other conditions.

Accordingly, it is an object of the present invention to provide compounds, compositions, and methods, for modulating cell signaling pathways and/or for inhibiting bromodomain proteins and epigenetic mechanisms including modulating the PI-3 kinase pathway by inhibiting PI-3 kinases, the methods, compounds, and compositions also useful for inhibiting cancerous tumor growth and for treating other diseases or conditions relating to aberrant PI3 kinase and/or bromodomain protein activity.

In another aspect the present invention relates to a pharmaceutical formulation comprising in association with a pharmaceutically acceptable carrier, diluent or excipient, a compound of Formulas I-VII (or a pharmaceutically acceptable salt thereof) as provided in any of the descriptions herein.

Compounds (or salts thereof) of the present invention are useful as an active ingredient in the manufacture of a medicament for use in inhibiting kinase activity, e.g., PI-3 kinase activity and/or for inhibiting a bromodomain protein(s).

The present invention also relates to a method of inhibiting kinase activity in a mammal including a human comprising administering to a mammal in need of treatment, a kinase inhibiting dose of a compound of Formulas I-VII or conjugate or prodrug thereof having any of the definitions herein.

The present invention further relates to a method of inhibiting PI-3 kinase comprising administering to a mammal in need of treatment, including a human, a PI-3 kinase-inhibiting dose of a compound of Formulas I-VII or conjugate or prodrug thereof having any of the definitions herein.

Further, the present invention provides a method of inhibiting tumor growth comprising administering to a mammal in need of treatment, including a human, an effective dose of a compound of Formulas I-VII, or conjugate or prodrug thereof, having any of the definitions herein.

In another aspect the invention relates to a method of modulating an epigenetic effect by regulating gene transcription in a cell comprising exposing a bromodomain containing protein to a compound of Formula I-VII.

In another aspect the present invention relates to a method of inhibiting bromodomain-mediated recognition of an acetyl lysine region of a protein comprising exposing the bromodomain to a compound of Formula I-VII.

In another aspect, the present invention relates to a method for treating a disease relating to aberrant PI3K activity by administering a compound of Formula I-VII.

In another aspect, the present invention relates to treating a disease relating to bromodomain protein activity by administering a compound of Formula I-VII.

In another aspect the invention relates to a method for treating a disease related to aberrant PI3K activity and bromodomain protein activity.

In another aspect the invention relates to methods for treating a disease including but not limited to cancer, non-cancer proliferation disease, sepsis, autoimmune disease, viral infection, atherosclerosis, Type 2 diabetes, obesity, inflammatory disease, and Myc-dependent disorder.

As an additional feature of the invention there is provided a pharmaceutical formulation comprising in association with a pharmaceutically acceptable carrier, diluent or excipient, a conjugate of a compound of Formulas I-VII (or of a pharmaceutically acceptable salt thereof) as provided in any of the descriptions herein.

These and other objects of the invention are evidenced by the summary of the invention, the description of the preferred embodiments and the claims.

DETAILED DESCRIPTION

Figure 1A:
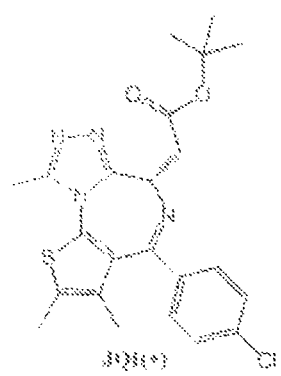
FIG. 1A provides the structure of known BET inhibitor JQ1(+).

A. Definitions.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatoses hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibrosdenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system:

skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant, lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; and breast cancer.

The term "cancerous cell" as provided herein, includes a cell affected by any one of the above-identified cancers.

As used herein, the term "branched" refers to a group containing from 1 to 24 backbone atoms wherein the backbone chain of the group contains one or more subordinate branches from the main chain. Preferred branched groups herein contain from 1 to 12 backbone atoms. Examples of branched groups include, but are not limited to, isobutyl, t-butyl isopropyl, —CH$_2$CH$_2$CH(CH$_3$)CH$_2$CH$_3$, —CH$_2$CH (CH$_2$ CH$_3$)CH$_2$ CH$_3$, —CH$_2$CH$_2$C(CH$_3$)$_2$CH$_3$, —CH$_2$CH$_2$C(CH$_3$)$_3$ and the like.

The term "unbranched" as used herein refers to a group containing from 1 to 24 backbone atoms wherein the backbone chain of the group extends in a direct line. Preferred unbranched groups herein contain from 1 to 12 backbone atoms.

The term "cyclic" or "cyclo" as used herein alone or in combination refers to a group having one or more closed rings, whether unsaturated or saturated, possessing rings of from 3 to 12 backbone atoms, preferably 3 to 7 backbone atoms.

The term "lower" as used herein refers to a group with 1 to 6 backbone atoms.

The term "saturated" as used herein refers to a group where all available valence bonds of the backbone atoms are attached to other atoms. Representative examples of saturated groups include, but are not limited to, butyl cyclohexyl, piperidine and the like.

The term "unsaturated" as used herein refers to a group where at least one available valence bond of two adjacent backbone atoms is not attached to other atoms. Representative examples of unsaturated groups include, but are not limited to, —CH$_2$ CH$_2$CH═CH$_2$, phenyl, pyrrole and the like.

The term "aliphatic" as used herein refers to an unbranched, branched or cyclic hydrocarbon group, which may be substituted or unsubstituted, and which may be saturated or unsaturated, but which is not aromatic. The term aliphatic further includes aliphatic groups, which comprise oxygen, nitrogen, sulfur or phosphorous atoms replacing one or more carbons of the hydrocarbon backbone.

The term "aromatic" as used herein refers to an unsaturated cyclic hydrocarbon group which may be substituted or unsubstituted having 4n+2 delocalized π(pi) electrons. The term aromatic further includes aromatic groups, which comprise a nitrogen atom replacing one or more carbons of the hydrocarbon backbone. Examples of aromatic groups include, but are not limited to, phenyl, naphthyl, thienyl, furanyl, pyridinyl, (is)oxazoyl and the like.

The term "substituted" as used herein refers to a group having one or more hydrogens or other atoms removed from a carbon or suitable heteroatom and replaced with a further group. Preferred substituted groups herein are substituted with one to five, most preferably one to three substituents. An atom with two substituents may be denoted with "di," whereas an atom with more than two substituents may be denoted by "poly." Representative examples of such substituents include, but are not limited to aliphatic groups, aromatic groups, alkyl, alkenyl, alkynyl, aryl, alkoxy, halo, aryloxy, carbonyl, acryl, cyano, amino, nitro, phosphate-containing groups, sulfur-containing groups, hydroxyl, alkylcarbonyloxy, arylcarbonyloxy, alkoxycarbonyloxy, aryloxycarbonyloxy, alkylcarbonyl, arylcarbonyl, alkoxycarbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl," "optionally substituted alkenyl," "optionally substituted alkynyl", "optionally substituted carbocyclic," "optionally substituted aryl," "optionally substituted heteroaryl," "optionally substituted heterocyclic," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, alkoxy, oxo, thiooxo, —NO2, —CN, CF3, N3, —NH2, protected amino, —NH-alkyl, —NH-alkenyl, —NH-alkynyl, —NH-cycloalkyl, —NH-aryl, —NHheteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)alkynyl, —C(O)-cycloalkyl, —C(O)-aryl, —C(O)-heteroaryl, —C(O)-heterocycloalkyl, —CONH2, —CONH-alkyl, —CONH-alkenyl, —CONH-alkynyl, —CONH-cycloalkyl, —CONH-aryl, —CONH-heteroaryl, —CONH-heterocycloalkyl, —OCO2-alkyl, —OCO2-alkenyl, —OCO2-alkynyl, —OCO2-cycloalkyl, —OCO2-aryl, —OCO2-heteroaryl, —OCO2-heterocycloalkyl, —OCONH2, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHCO(O)-cycloalkyl, —NHC(O)-aryl, —NHC(O)-heteroaryl, —NHC(O)-heterocycloalkyl, —NHCO2-alkyl, —NHCO2-alkenyl, —NHCO2-alkynyl, —NHCO2-cycloalkyl, —NHCO2-aryl, —NHCO2-heteroaryl, —NHCO2-heterocycloalkyl, —NHC(O)NH2, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, NHC(S)NH2, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)NH2, —NHC(NH)NHalkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl, —SO2NH2'—SO2NH-alkyl, —SO2NH-alkenyl, —SO2NH-alkynyl, —SO2NH-cycloalkyl, —SO2NH-aryl, —SO2NH-heteroaryl, —SO2NHheterocycloalkyl, —NHSO2-alkyl, —NHSO2-alkenyl, —NHSO2alkynyl, —NHSO2-cycloalkyl, —NHSO2-aryl, —NHSO2heteroaryl, —NHSO2-heterocycloalkyl, —CH2NH2, —CH2SO2CH3-alkyl, -alkenyl, -alkynyl, -aryl, -arylalkyl, -heteroaryl, -heteroarylalkyl, -heterocycloalkyl, -cycloalkyl, -carbocyclic, -heterocyclic, poly-alkoxyalkyl, polyalkoxy, methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

The term "unsubstituted" as used herein refers to a group that does not have any further groups attached thereto or substituted therefore.

The term "alkyl" as used herein, alone or in combination, refers to a branched or unbranched, saturated aliphatic group. The alkyl radical may be optionally substituted independently with one or more substituents described herein. Lower alkyl refers to alkyl groups of from one to six carbon atoms. Examples of lower alkyl groups include methyl, ethyl, propyl, isopropyl, butyl, s-butyl, t-butyl, isobutyl, pentyl, and the like. Higher alkyl refers to alkyl groups containing more than seven carbon atoms. Exemplary alkyl groups are those of $C_{20}$ or below. In this application, alkyl refers to alkanyl, alkenyl, and alkynyl residues (and combinations thereof); it is intended to include vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl. Representative examples of alkyl groups include, but are not limited to, methyl, ethyl, n-propyl, isopropyl, n-butyl, isobutyl, sec-butyl, tert-butyl, octyl, decyl, tetradecyl, hexadecyl, eicosyl, tetracosyl and the like. The terms "alkyl" or "alk" as used herein refer to a saturated linear or branched-chain monovalent hydrocarbon radical of one to twelve carbon atoms ($C_2$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)$ $CH_2CH_3$), 2-methyl-2-propyl (t-Bu, t-butyl, —$C(CH_3)_3$), 1-pentyl, (n-pentyl, —$CH_2CH_2CH_2CH_2CH_3$), 2-pentyl (—$CH(CH_3)CH_2CH_2CH_3$), 3--pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1--butyl (—$CH_2CH(CH_3)CH_2CH_3$), 1-hexyl (—$CH_2CH_2CH_2CH_2CH_2CH_3$), 2--hexyl (—$CH(CH_3)CH_2CH_2CH_2CH_3$), 3-hexyl (—$CH(CH_2CH_3)(CH_2CH_2CH_3)_2$), 2-methyl-2--pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3--pentyl (—$CH(CH_2CH_3)CH(CH_3)_2$), 2,3-dimethyl-2-butyl (—$C(CH_3)_2CH(CH_3)_2$), 3,3-dimethyl-2--butyl (—$CH(CH_3)$ $C(CH_3)_3$, 1-heptyl, 1-octyl, and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring, or 7 to 12 carbon atoms as a bicyclic ring. The cycloalkyl radical may be optionally substituted independently with one or more substituents described herein. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "alkenyl" as used herein alone or in combination refers to a branched or unbranched, unsaturated aliphatic group containing at least one carbon-carbon double bond which may occur at any stable point along the chain. The alkenyl radical may be optionally substituted independently with one or more substituents described herein, and includes radicals having "cis" and "trans" orientations, or alternatively, "E" and "Z" orientations. Representative examples of alkenyl groups include, but are not limited to, ethenyl, E- and Z-pentenyl, decenyl and the like.

The term "alkynyl" as used herein alone or in combination refers to a branched or unbranched, unsaturated aliphatic group containing at least one carbon-carbon triple bond which may occur at any stable point along the chain.

The alkynyl radical may be optionally substituted independently with one or more substituents described herein. Representative examples of alkynyl groups include, but are not limited to, ethynyl, propynyl, propargyl, butynyl, hexynyl, decynyl and the like.

The term "aryl" as used herein alone or in combination refers to a substituted or unsubstituted aromatic group, which may be optionally fused to other aromatic or non-aromatic cyclic groups. Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The term "alkoxy" as used herein alone or in combination refers to an alkyl, alkenyl or alkynyl group bound through a single terminal ether linkage. Examples of alkoxy groups include, but are not limned to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy.

The terms "heteroaryl" and "heteroar-", used alone or as part of a larger moiety, e.g., "heteroaralkyl", or "heteroaralkoxy", refer to groups having 5 to 18 ring atoms, preferably, 5, 6, or 9 ring atoms; having 6, 10, or 14 pi ($\pi$)electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heyeroaryl may be a single ring, or two or more fused rings. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

The term "aryloxy" as used herein alone or in combination refers to an aryl group bound through a single terminal ether linkage.

The terms "halogen", "halo" and "hal" as used herein refer to monovalent atoms of fluorine, chlorine, bromine, iodine and astatine.

The term "hetero" or "heteroatom" as used herein refers to a group that includes one or more atoms of any element other than carbon or hydrogen. Representative examples of hetero groups include, but are not limited to, those groups that contain heteroatoms including, but not limited to, nitrogen, oxygen, sulfur and phosphorus.

The term "heterocycle" or "heterocyclyl" or "heterocyclic ring" or "heterocyclic" as used herein refers to a cyclic group containing a heteroatom in a 3 to 7-membered ring moiety. The heterocyclic radical may be optionally substituted independently with one or more substituents described herein. Representative examples of heterocycles include, but are not limited to, pyridine, piperadine, pyrimidine, pyridazine, piperazine, pyrrole, pyrrolidinone, pyrrolidine, morpholine, thiomorpholine, indole, isoindole, imidazole, triazole, tetrazole, furan, benzofuran, dibenzofuran, thiophene, thiazole, benzothiazole, benzoxazole, benzothiophene, quinoline, isoquinoline, azapine, naphthopyran, furanobenzopyranone and the like.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

The term "substituent" means any group including but not limited to H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, halo, haloalkyl, haloalkoxy, hydroxy, oxo (valency rules permitting), lower alkanyl, lower alkenyl, lower alkynyl, alkoxy, optionally substituted cycloalkyl, optionally substituted heterocycloalkyl, optionally substituted aryl, optionally substituted heteroaryl, alkylaminoalkyl, dialkylaminoalkyl, carboxy, carboxy ester, —C(O)NR$^5$R" (where R$^5$ is hydrogen or alkyl and R" is hydrogen, alkyl, aryl, or heterocyclyl), —NR$^5$C(O)R" (where R$^5$ is hydrogen or alkyl and R" is alkyl, aryl, or heterocyclyl), amino, alkylamino, dialkylamino, and —NHS(O)$_2$R' (where R' is alkyl, aryl, or heteroaryl).

The term "carbonyl" "carboxy" as used herein alone or in combination refers to a group that contains a carbon-oxygen double bond. Representative examples of groups which contain a carbonyl include, but are not limited to, aldehydes (i.e., formyls), ketones (i.e., acyls), carboxylic acids (i.e., carboxyls), amides (i.e., amidos), imides (i.e., imidos), esters, anhydrides and the like.

The term "carbamate" as used herein alone or in combination refers to an ester group represented by the general structure —NH(CO)O—. Carbamate esters may have alkyl or aryl groups substituted on the nitrogen, or the amide function.

The term "cyanate" "isocyanate", "thiocyanate", or "isothiocyanate" as used herein alone or in combination refers to an oxygen- or sulfur-carbon double bond carbon-nitrogen double bond. Representative examples of cyano groups include, but are not limited to, isocyanate, isothiocyanate and the like.

The term "cyano", "cyanide", "isocyanide", "nitrile", or "isonitrile" as used herein alone or in combination refers to a carbon-nitrogen triple bond.

The term "amino" as used herein alone or in combination refers to a group containing a backbone nitrogen atom. Representative examples of amino groups include, but are not limited to, alkylamino, dialkylamino, arylamino, diarylamino, alkylarylamino, alkylcarbonylamino, arylcarbonylamino, carbamoyl, ureido and the like.

The term "phosphate-containing group" as used herein refers to a group containing at least one phosphorous atom in an oxidized state. Representative examples include, but are not limited to, phosphonic acids, phosphinic acids, phosphate esters, phosphinidenes, phosphinos, phosphinyls, phosphinylidenes, phosphos, phosphonos, phosphoranyls, phosphoranylidenes, phosphorosos and the like.

The term "sulfur-containing group" as used herein refers to a group containing a sulfur atom. Representative examples include, but are not limited to, sulfhydryls, sulfenos, sulfinos, sulfinyls, sulfos, sulfonyls, thios, thioxos and the like.

The term "optional" or "optionally" as used herein means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and substituted alkyl.

The term "targeting agent" as used herein means any moiety whose attachment to a compound of the invention allows the increase in concentration of the compound at a site of treatment, for example, a tumor site. Exemplary targeting agents include but are not limited to carbohydrates, peptides, vitamins, and antibodies.

The term "effective amount" or "effective concentration" or "therapeutically effective amount" when used in reference to a compound, product, or composition as provided herein, means a sufficient amount of the compound, product or composition to provide the desired result, e.g. pharmaceutical or therapeutic effect. The exact amount required will vary depending on the particular compound, product or composition used, its made of administration, and the like. Thus, it is not always possible to specify an exact "effective amount." However, an appropriate effective amount may be determined by one of ordinary skill in the art informed by the instant disclosure using only routine experimentation.

The term "hydrolyzable" as used herein refers to whether the group is capable of or prone to hydrolysis (i.e., splitting of the molecule or group into two or more new molecules or groups).

The term "prodrug" or "procompound" as used in this application refers to a precursor or derivative form of a compound of the invention that may be less active, e.g. cytotoxic, to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "signal modulation" refers generally to an alteration of activity, for example, inhibition of one or more components of a signaling pathway or downstream target by an agent(s) that can be administered for beneficial therapeutic effect, e.g. tumor growth inhibition, cancer treatment, etc.

The term "conjugate" as used herein refers to a compound that has been formed by the joining of two or more compounds via either a covalent or non-covalent bond including also the attachment of compounds of the invention to proteins and antibodies.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "metabolite" is a product produced through metabolism in the body of a specified compound or salt thereof. Metabolites of a compound may be identified using routine techniques known in the art and their activities determined using any suitable test such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "pharmaceutically acceptable salt" of a compound of the instant invention (e.g., Formula I) is one which is the acid addition salt of a basic compound of the invention with an inorganic or organic acid which affords a physiologically acceptable anion or which is the salt formed by an acidic compound of the invention with a base which affords a physiologically acceptable cation.

The phrase "pharmaceutically acceptable salt" as used herein, also refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If a compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If a compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect one or more functional groups on the compound. For example, an "aminoprotecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ehtyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention" and "compounds of the present invention" include compounds of Formulas I-VII and stereoisomers, geometric isomers, tautomers, solvates, metabolites, and pharmaceutically acceptable salts, prodrugs, and conjugates thereof.

B. Compounds

In one aspect, the present invention relates to a compound of Formula I or a pharmaceutically acceptable salt thereof.

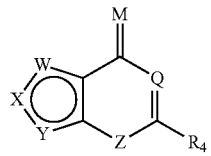

Formula I

Wherein Z is O or NR3;

Q is N;

M is O or S;

W is N, S, or CR1

X is N or CR1;

Y is NR2 or CR3;

R1, R2, R3, and R4 are each independently selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boromic acid, and boronic ester, azo, substituted azo, azido, nitroso, imino, substituted imino, oxime, substituted oxime, alkoxy, substituted alkoxy, aryloxy, substituted aryloxy, thioether, substituted thioether, carbamate, and substituted carbamate.

In another embodiment, the present invention provides compounds of the Formulas II-IV:

Formula II

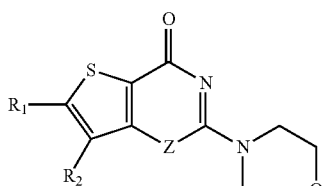

Z = O, NR₃

Formula III

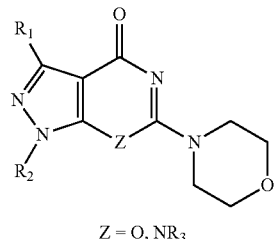

Z = O, NR₃

Formula IV

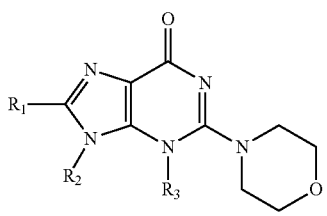

wherein R1, R2, and R3 are each independently selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate.

Alternatively, Formulas II-IV wherein R1, R2, and R3 are selected from any subset of 2, 3, 4, 5, 6, 7, or 8 of substituents selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, and boronic ester, azo, substituted azo, azide, nitroso, imino, substituted imino, oxime, substituted oxime, alkoxy, substituted alkoxy, aryloxy, substituted aryloxy, thioether, substituted thioether, carbamate, substituted carbamate.

In another aspect, the present invention provides compounds of Formula V-VII or a pharmaceutically acceptable salt thereof:

Formula V

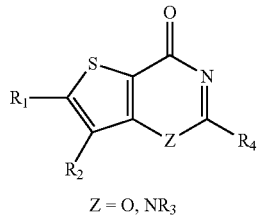

Z = O, NR₃

Formula VI

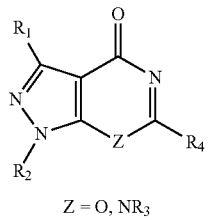

Z = O, NR₃

Formula VII

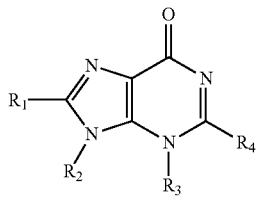

wherein R1, R2, R3, and R4 are each independently selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphoric acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, and boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate.

Alternatively, Formulas V-VII wherein R1, R2, and R3 are selected from any subset of 2, 3, 4, 5, 6, 7, or 8 of the substituents selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, and boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate.

A pharmaceutically acceptable salt of a compound of the instant invention is one which is the acid addition salt of a basic compound of Formulas I-VII with an inorganic or organic acid which affords a physiologically acceptable anion, or which is the salt formed by an acidic compound of Formulas I-VII with a base which affords a physiologically acceptable cation and provides a particular aspect of the invention. Examples of such acids and bases are provided herein below. For example, a basic compound of the invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

The present invention also includes isotopically-labelled compounds, and pharmaceutically acceptable salts thereof, which are identical to those recited in Formulas I-VII, but replace one or more atoms by a corresponding isotope. Examples of isotopes that can be incorporated into compounds of the invention include isotopes of hydrogen, carbon, nitrogen, oxygen, phosphorous, fluorine and chlorine. Compounds of the present disclosure, conjugates thereof, and pharmaceutically acceptable salts of said compounds or of said conjugates which contain the aforementioned isotopes and/or other isotopes of other atoms are within the scope of this disclosure. Certain isotopically-labelled compounds of the present disclosure, for example those into which radioactive isotopes such as $^3$H and $^{14}$C are incorporated, are useful in drug and/or substrate tissue distribution assays for example when imaging tumors. Fluorine-18 ($^{18}$F) is particularly preferred for ease of preparation and detectability. Isotopically labeled compounds of the invention can generally be prepared by carrying out the procedures disclosed in the Schemes and/or in the Examples and Preparations below, by substituting a readily available isotopically labeled reagent for a non-isotopically labeled reagent.

It will be appreciated that certain compounds of Formulas I-VII (or salts, procompounds/prodrugs, or conjugates, etc.) may exist in, and be isolated in, isomeric forms, including tautomeric forms, cis- or trans-isomers, as well as optically active, racemic, or diastereomeric forms. It is to be understood that the present invention encompasses a compound of Formulas I-VII in any of the tautomeric forms or as a mixture thereof, or as a mixture of diastereomers, as well as in the form of an individual diastereomer, and that the present invention encompasses a compound of Formulas I-VII as a mixture of enantiomers, as well as in the form of an individual enantiomer, any of which mixtures or form possesses inhibitory properties against kinases including PI-3 kinase, it being well known in the art how to prepare or isolate particular forms and how to determine inhibitory properties against kinases by standard tests including those described herein below.

In addition, a compound of Formulas I-VII (or salt, procompound/prodrug, or conjugate thereof, etc.) may exhibit polymorphism or may form a solvate with water or an organic solvent. The present invention also encompasses any such polymorphic form, any solvate or any mixture thereof.

D.1. Synthesis of Compounds of the Invention

The compounds of the present invention may be prepared by processes known in the chemical art. Starting materials and intermediates used to prepare a compound of the invention are either commercially available or can be prepared by one of ordinary skill in the art.

The compounds of the invention, or their pharmaceutically acceptable salts, may have asymmetric carbon atoms or quaternized nitrogen atoms in their structure. It will be appreciated that certain compounds of Formulas I-VII (or salts, conjugates, etc.) may exist in, and be isolated in, isomeric forms, including tautomeric forms, cis- or trans-isomers, as well as optically active, racemic, or diastereomeric forms. It is to be understood that the present invention encompasses a compound of Formulas I-VII in any of the tautomeric forms or as a mixture thereof; or as a mixture of diastereomers, as well as in the form of an individual diastereomer, and that the present invention encompasses a compound of Formulas I-VII as a mixture of enantiomers, as well as in the form of an individual enantiomer, any of which mixtures or form possesses inhibitory properties against kinases, for example PI-3 kinases and/or bromodomain proteins. The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of the invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using other conventional techniques. For example, enantiomers (R- and S-isomers) may be resolved by formation of diastereoisomeric salts or complexes which may be separated, for example, by crystallization; via formation of diastereoisomeric derivatives which may be separated, for example, by crystallization; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts or solvents or by converting an enantiomer to the other by asymmetric transformation. For a mixture of enantiomers, enriched in a particular enantiomer, the major component enantiomer may be further enriched (with concomitant loss in yield) by recrystallization.

A compound of Formula II in which R1 is hydrogen, Z is O, and R2 has the meaning defined hereinabove may be synthesized as illustrated by Scheme 1.

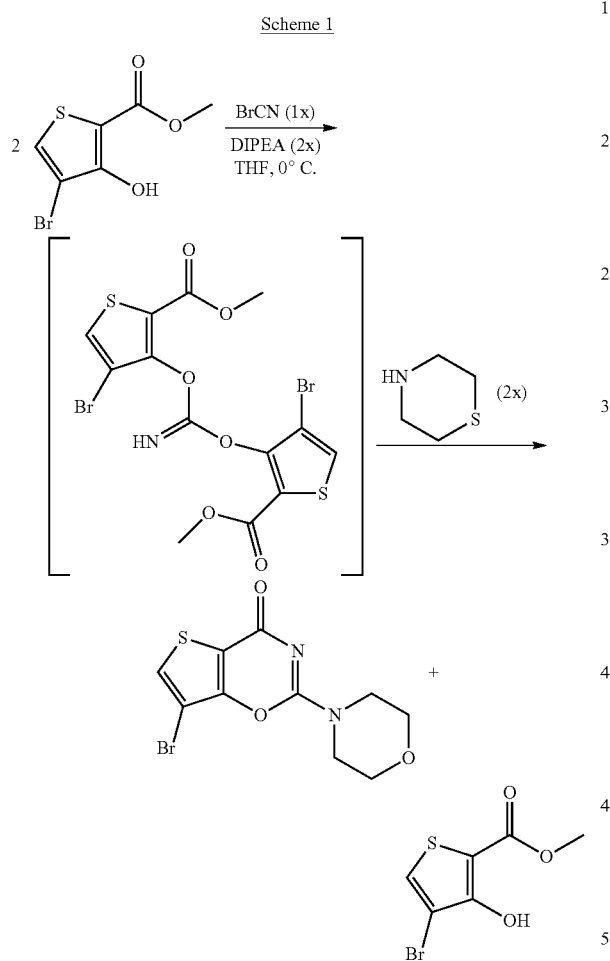

A compound of Formula III in which Z=O, and R1, R2 and R3 have the meanings defined hereinabove may be synthesized as illustrated by Scheme 2.

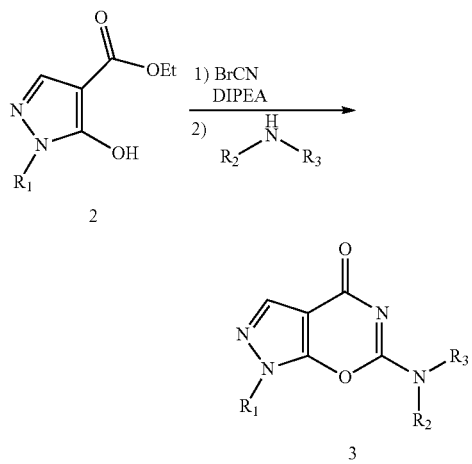

Another route to make a compound of Formula III in which Z=N—R3, and R1 and R3 are hydrogen and R2 has the meaning defined herein above may be synthesized as illustrated by Scheme 3.

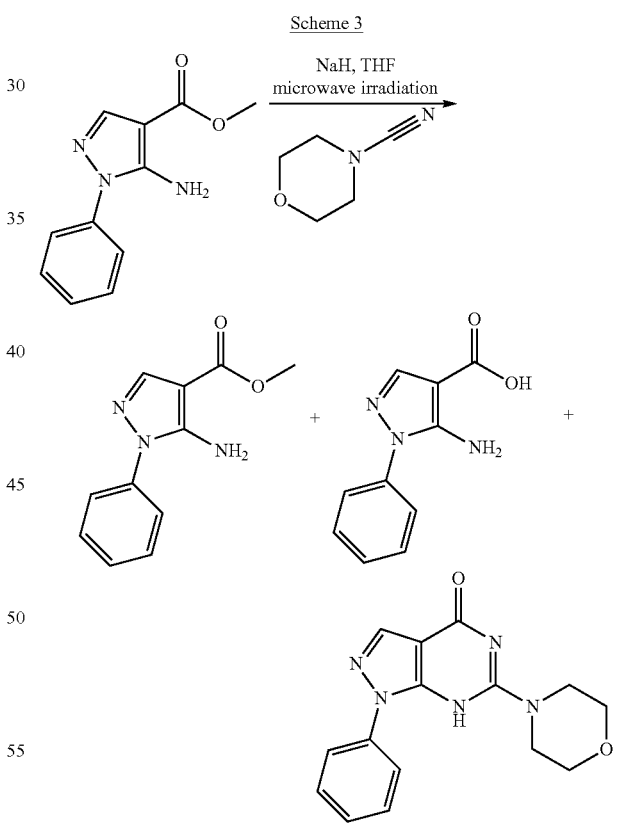

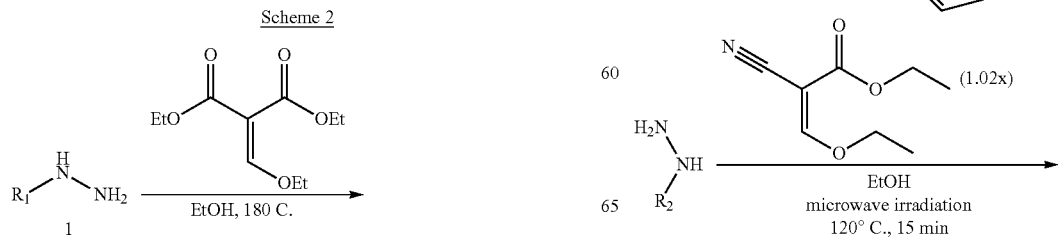

-continued

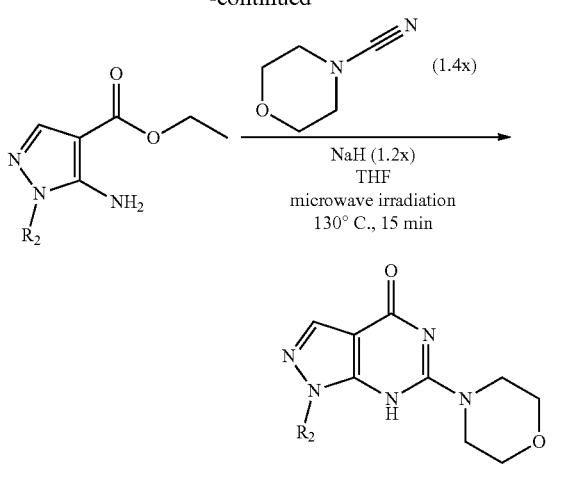

Another route to make a compound of Formula II in which R1, R2 and R3 are hydrogen and Z is NR3 is illustrated by Scheme 4.

Scheme 4

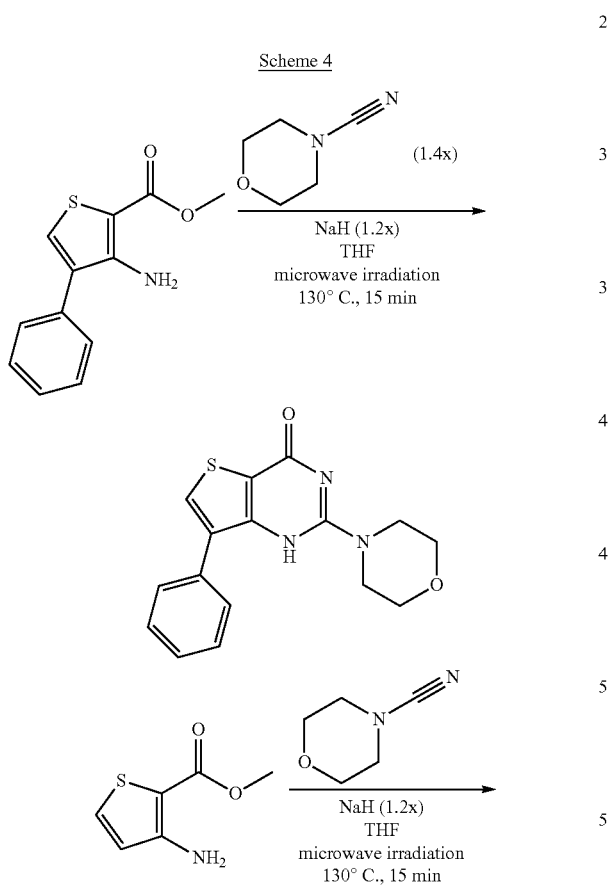

A compound of Formula IV in which R1 and R3 are hydrogen and R2 is —CH$_2$(phenyl) may be synthesized as illustrated by Scheme 5.

Scheme 5

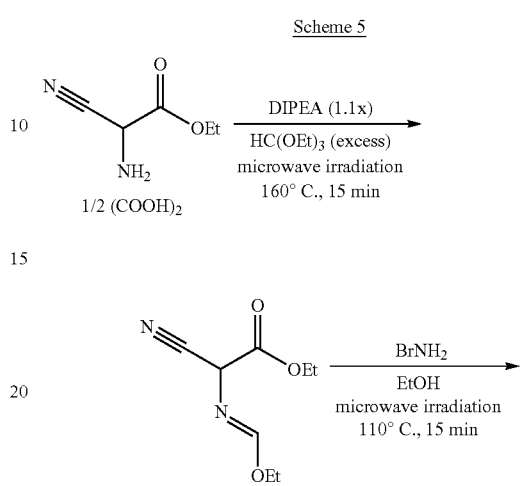

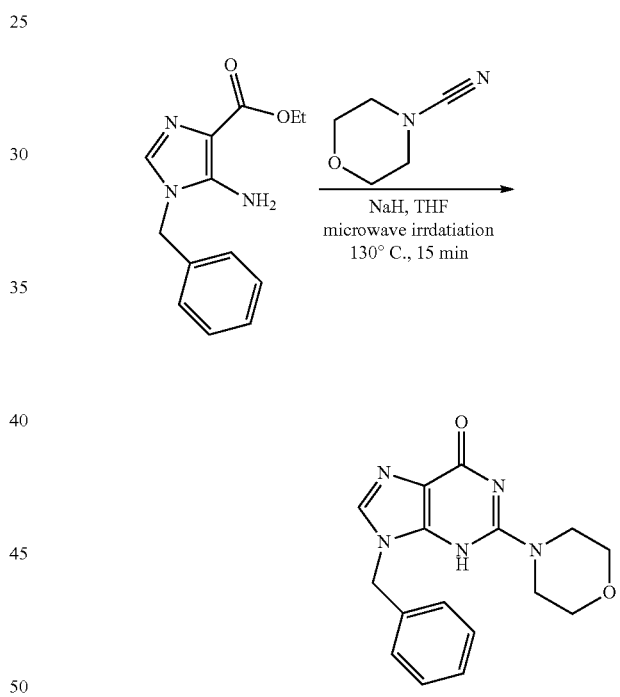

A compound of Formula V in which R1 is hydrogen, Z is O, and R2 has the meaning defined hereinabove may be synthesized as illustrated by Scheme 6.

Scheme 6

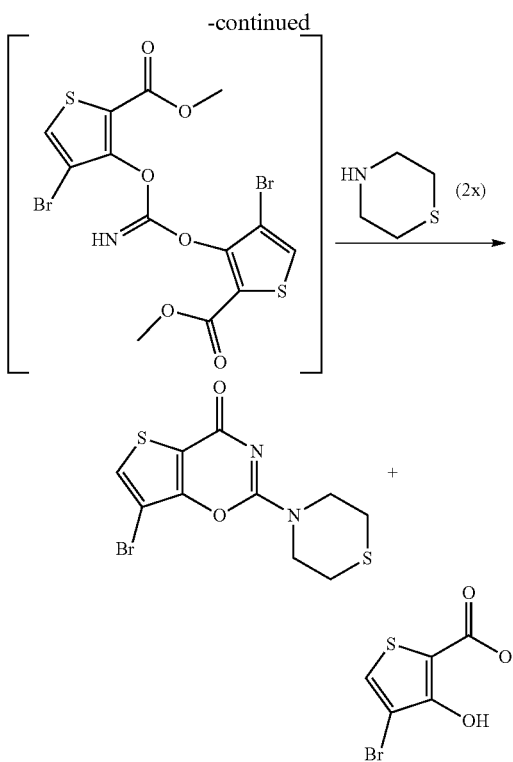

A compound of Formula VI in which Z=O, and R1, R2 and R3 have the meanings defined hereinabove may be synthesized as illustrated by Scheme 7.

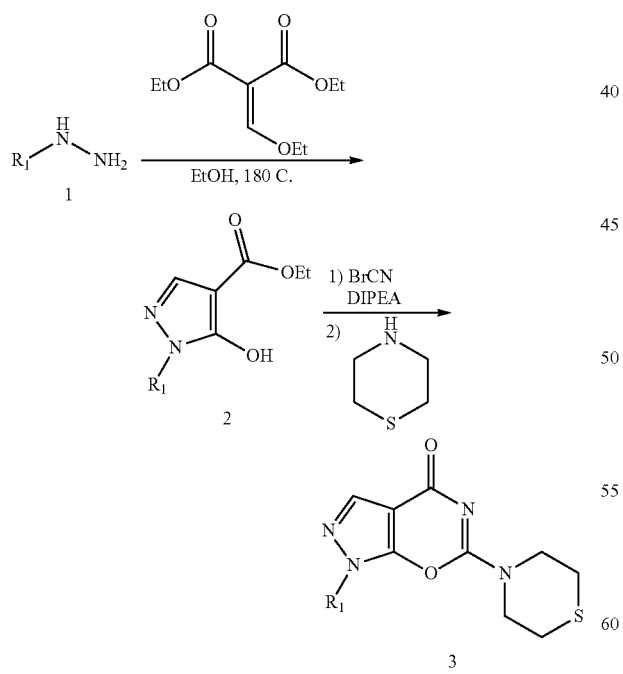

Another route to make a compound of Formula VI in which Z=N—R3, and R1 and R3 are hydrogen and R2 has the meaning defined herein above may be synthesized as illustrated by Scheme 8.

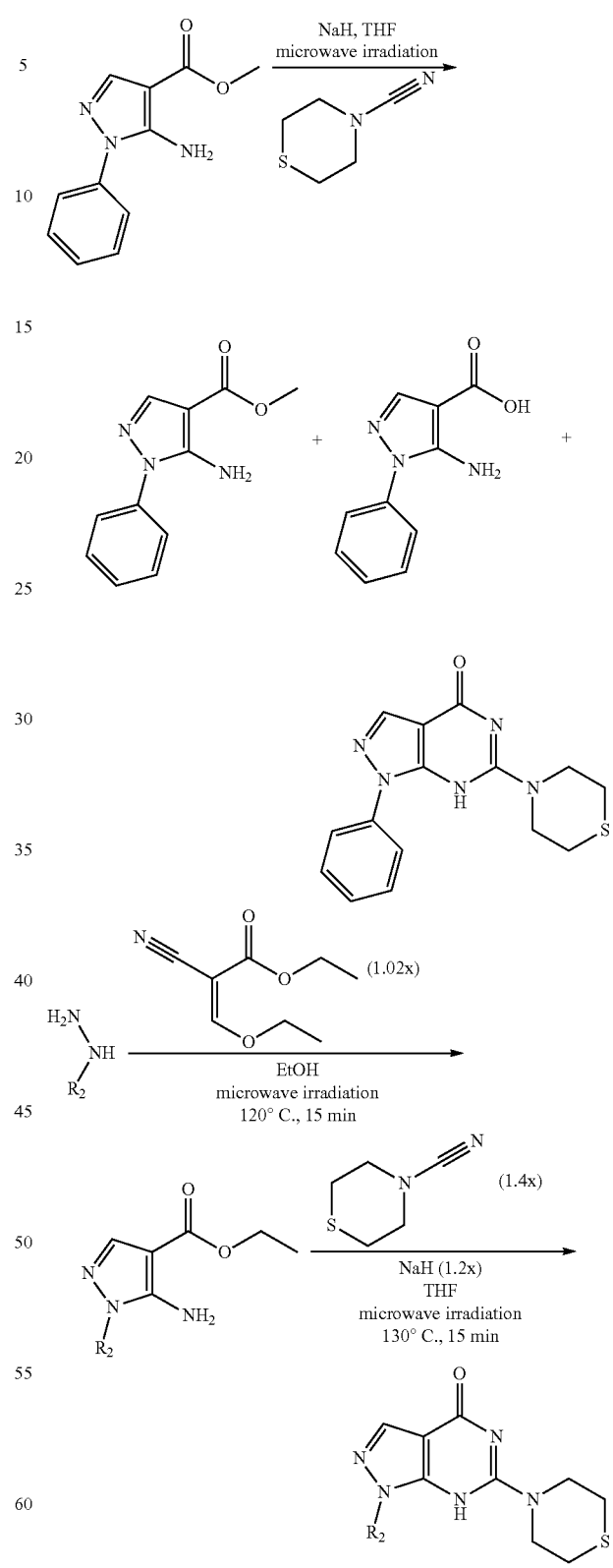

Another route to make a compound of Formula V in which R1, R2 and R3 are hydrogen and Z is NR3 is illustrated by Scheme 9.

Scheme 9

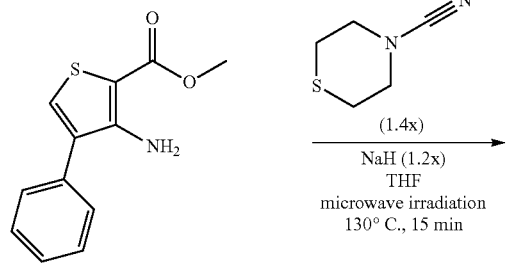

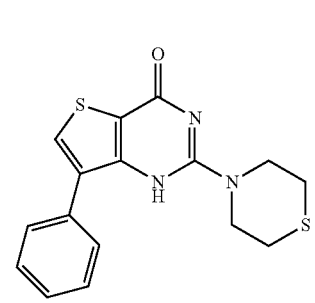

A compound of Formula VII in which R1 and R3 are hydrogen and R2 is —CH₃(phenyl) may be synthesized as illustrated by Scheme 10.

Scheme 10

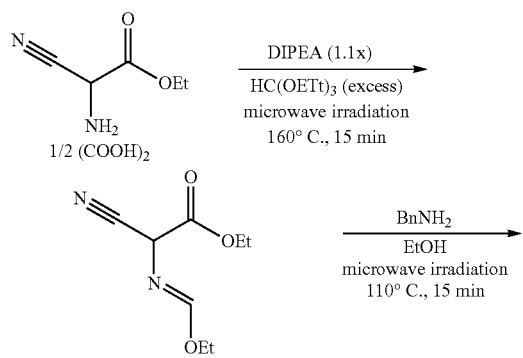

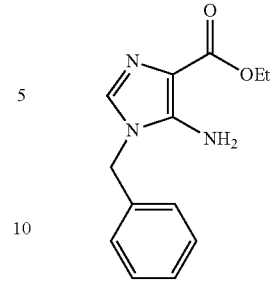

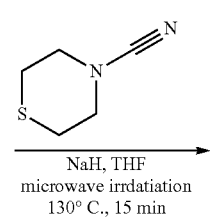

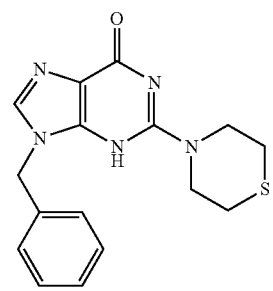

In Schemes 6-10 above additional compounds of Formula V, VI, and VII may be synthesized by replacing the thiomorpholine reagent with an amino-containing group such as but not limited to:

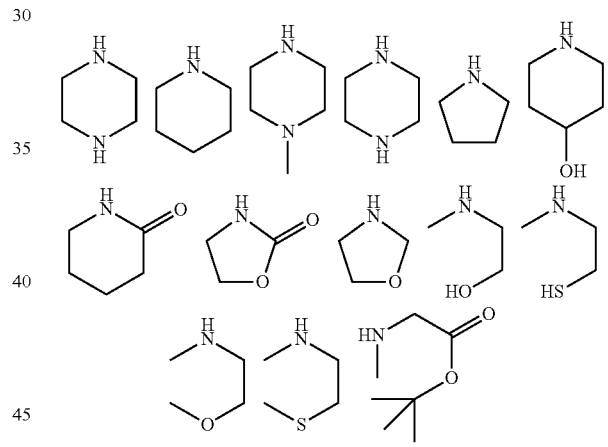

In Schemes 6-10 additional compounds of Formula V, VI, and VII may be synthesized by substituting the cyano-thiomorpholine in the reagents for reagents containing other cyano-amino groups such as but not limited to:

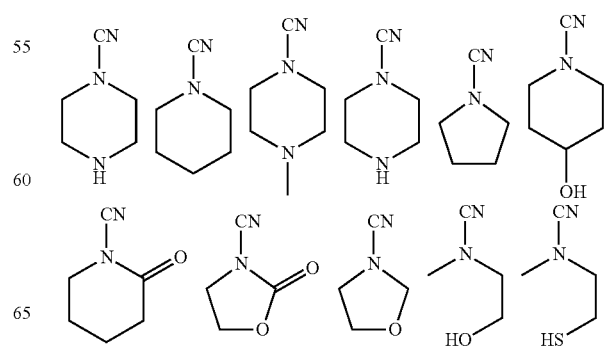

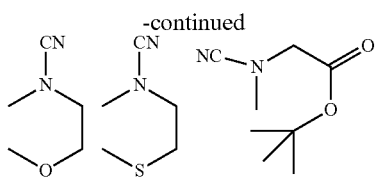

For cyano-amines (cyanamides) that are not commercially available they are readily prepared from the corresponding amine by reaction with cyanogen bromide or cyanogen chloride or using more recent techniques going through a dithiocarbamic acid intermediate (H. Ghosh et al., Tetrahedron Letters 2009, 50, 2407-2410). All of the compounds of Formula I-VII containing the chromone carbonyl may be converted to the thione analog by exposure to Lawasson's reagent using conditions described by G. Morales, J. Med. Cheam. 2013, 56, 1922-1939.

E. Formulations

An additional aspect of the invention provides a pharmaceutical formulation or composition comprising in association with a pharmaceutically acceptable carrier, diluent or excipient, a compound of the invention, e.g. Formulas I-VII (or a pharmaceutically acceptable salt or procompound or conjugate thereof) as provided in any of the descriptions herein. Compositions of the present invention may be in the form of tablets or lozenges formulated in a conventional manner. For example, tablets and capsules for oral administration may contain conventional excipients including, but not limited to, binding agents, fibers, lubricants, disentegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions of the present invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions of the present invention may also be formulated as suppositories, which may contain suppository bases including, but not limited to, cocoa butter or glycosides. Compositions of the present invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane.

Compositions of the present invention may also be formulated as transdermal formulations comprising aqueous or nonaqueous vehicles including, but not limited to, creams, ointments, lotions, pastes, medicated plaster, patch, or membrane.

Compositions of the present invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of the present invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of the present invention may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al., or U.S. Pat. No. 4,508,703 of Redziniak et al., can be used. Other suitable formulations can employ niosomes. Niosomes are lipid vesicles similar to liposomes, with membranes consisting largely of non-ionic lipids, some forms of which are effective for transporting compounds across the stratum corneum.

The following formulation examples are illustrative only and are not intended to limit the scope of the invention in any way. The phrase "active ingredient" refers herein to a compound according to Formulas I-VII or a pharmaceutically acceptable salt, procompound, conjugate, or solvate thereof.

| Formulation 1: Tablet containing the following components: | |
|---|---|
| Ingredient | Amount (mg/tablet) |
| Active ingredient | 250 |
| Dried starch | 200 |
| Magnesium stearate | 10 |
| Total | 460 mg |

| Formulation 2: Capsules containing the following components: | |
|---|---|
| Ingredient | Amount (mg/tablet) |
| Active ingredient | 60 |
| Dried starch | 44 |
| Magnesium stearate | 1.5 |
| Microcrystalline cellulose | 44 |
| Total | 150 mg |

Parenteral dosage forms for administration to patients by various routes including, but not limited to, subcutaneous, intravenous (including bolus infection), intramuscular, and intraarterial are also contemplated by the present invention. Parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

An example parenteral composition of the invention intended for dilution with aqueous solution(s) comprises for example 5% Dextrose Injection, USP, or 0.9% Sodium Chloride Injection, USP, prior to administration to a patient, and is an aqueous solution that comprises irinotecan, sorbitol NF powder, and lactic acid, USP, and has a pH of from about 3.0 to about 3.8 or from 3.0 to 3.8.

F. Therapeutic Use

Compounds and compositions described herein are generally useful for the inhibition of activity of PI3K and/or one or more proteins involved in epigenetic regulation mediated by bromodomain proteins.

In one embodiment the invention provides a method of modulating the PI3K pathway by inhibiting PI3K.

In another embodiment the invention provides a method to modulate epigenetic regulation in a cell mediated by bromodomains (e.g., BET proteins, such as BRD2, BRD3, BRD4, and/or BRDT, and non-BET proteins, such as CBP, ATAD2A, GCN5L, BAZ2B, FALZ, TAF1, and/or BRPF1), by administering a compound as described herein. In some embodiments, the compounds described herein are capable of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a biological sample useful for purposes including, but are not limited to, blood transfusion, organ-transplantation, biological specimen storage, and biological assays.

In some embodiments, the present invention provides a method of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a patient comprising the step of administering to said patient a compound or composition of the invention.

The present invention further relates to methods of treating diseases and conditions associated with aberrant kinase and/or bromodomain activity by administering a therapeutically effective amount of one or more compounds of Formulas I-VII. The compounds of the invention act as inhibitors of kinase activity and/or bromodomain proteins thereby providing a therapeutic method for treating conditions relating to such defects.

Inhibitory activity can be determined routinely using known methods. For example, in vitro kinase inhibition (e.g., PI3K inhibition) can be detected by a standard kinase inhibition assay using labeled ATP to determine if a test compound inhibits the transfer of phosphate from ATP to the kinase substrate. In vivo, PI3K inhibition can be determined from target tissue biopsies by standard tissue processing to disrupt cells and then performing Western Blot analysis to determine the presence or absence of pAKT (substrate of PI3K) relative to a control sample.

The activity of a compound of the invention as an inhibitor of a bromodomain-containing protein, such as a BET protein, such as BRD2, BRD3, BRD4, and/or BRDT, or an isoform or mutant thereof, may be determined in vitro, in vivo, or in a cell line. In vitro assays include assays that determine inhibition of bromodomain-containing proteins. Alternatively, inhibitor binding may be determined by running a competition experiment where a provided compound is incubated with a bromodomain-containing protein, such as a BET protein bound to known ligands, labeled or unlabeled. For example, bromodomain inhibition can be determined in vitro using Alpha Screen Technology (http://www.reactionbiology.com/webapps/site/NewsPDFs/Bromodomain%20Assay%20Platform%20for%20Drug%20Screening%20and%20Discovery.pdf). In vivo bromodomain inhibition can be determined indirectly by evaluating the amount of protein present of proteins whose genes' transcription is influenced or controlled by the bromodomain protein, for example, the MYCN protein transcription is controlled by BRD4 (J. E. Delmore et al., Cell, 2011, 146, 904-917; A. Puissant, Cancer Discov. 2013, 3, 308-323). Bromodomain inhibition may also be predicted by in silico modeling as described below in the Examples.

In certain embodiments, the invention provides a method of treating a disorder (as described above) in a subject, comprising administering to the subject identified as in need thereof, a compound of the invention. The identification of those patients who are in need of treatment for the disorders described herein is within the ability and knowledge of one skilled in the art. Certain of the methods for identification of patients who are at risk of developing the above disorders which can be treated by the subject method are appreciated in the medical arts, such as family history, and the presence of risk factors associated with the development of that disease state in the subject patient.

Assessing the efficacy of a treatment in a patient includes determining the pre-treatment extent of a disorder by methods known in the art (e.g., determining tumor size or screening for tumor markers where the cell proliferative disorder is cancer), then administering a therapeutically effective amount of a compound of the invention, to the patient. After an appropriate period of time after administration (e.g., 1 day, 1 week, 2 weeks, one month, six months), the extent of the disorder is again determined. Modulation (e.g., decrease) of the extent or invasiveness of the disorder (e.g. reduced tumor size) would indicate efficacy of the treatment. The extent or invasiveness of the disorder may be determined periodically throughout treatment. For example, the extent or invasiveness of the disorder may be assessed every few hours, days or weeks to assess the further efficacy of the treatment. A decrease in extent or invasiveness of the disorder indicates that the treatment is efficacious. The methods described may be used to screen or select patients that may benefit from treatment with a compound of the invention.

The present invention encompasses medical use of compounds of Formula I-VII including methods of treatment of a patient suffering from a condition or disease associated with aberrant kinase activity, including PI-3 kinase, or with MYC (c-MYC or MYCN) driven disease, or any disease abated by the use of a bromodomain inhibitor. For example, kinase activity may be aberrant by being excessive, or constitutively active in a patient in need of such treatment. Exemplary, but non-exclusive diseases and adverse conditions relating to aberrant kinase activity, in particular PI-3 kinase signaling activity, have been disclosed in the art, for example U.S. 2002/0150954A1; U.S. Pat. Nos. 5,504,103; 6,518,277B1; 6,403,588; 6,482,623; 6,518,277, 6,667,300, U.S. 20030216389; U.S.20030195211; U.S.20020037276 and U.S. Pat. No. 5,703,075 the contents of which are herein incorporated by reference.

In one aspect, the present invention relates to a method for treating inflammatory disease comprising administering to a patient in need thereof a therapeutically effective amount of a compound or compounds of Formula I-VII.

In another aspect, methods of the invention can be applied in the treatment of CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; and attention deficit/hyperactivity disorder (ADHD).

In another aspect, the present invention provides a method for treating Alzheimer's Disease comprising administering to a patient in need thereof a therapeutically effective amount of a compound of Formula I-VII. It has been reported that increasing PIP2 concentrations by, for example, inhibiting PI-3 kinase decreases levels of neurotoxins associated with Alzheimer's Disease (US 2008/0312187; incorporated herein by reference).

In another aspect, the present invention provides a method for enhancing the chemosensitivity of tumor cells comprising administering to a patient in need thereof a therapeutically effective amount of a compound of Formula I-VII.

In another aspect, the present invention provides a method for enhancing the radiosensitivity of tumor cells comprising administering to a patient in need thereof a therapeutically effective amount of a compound of Formula I-VII.

In another aspect, the present invention provides a method for inhibiting or reducing tumor growth comprising administering to a patient in need thereof a therapeutically effective amount of a compound of a compound of Formula I-VII.

In another aspect, the present invention provides a method for inducing oxidative stress in tumor cells comprising administering to a patient in need thereof a therapeutically effective amount of a compound of Formula I-VII.

In another aspect, the present invention provides a method for inhibiting or reducing tumor growth by inhibiting cancer stem cell growth and/or proliferation comprising administering to a patient in need thereof a therapeutically effective amount of a compound of Formula I-VII.

In another aspect, the present invention provides a method for inhibiting tumor induced angiogenesis comprising administering to a patient in need thereof a therapeutically effective amount of a compound of Formula I-VII.

Further, the present invention provides a method for inhibiting angiogenesis associated with non-cancer diseases comprising administering to a patient in need thereof a therapeutically effective amount of a compound of Formula I-VII.

In yet another aspect, the present invention provides a therapeutic method for increasing apoptosis in cancer cells and cancerous tumors comprising administering to a patient in need thereof a therapeutically effective amount of a compound of Formula I-VII.

The present invention also provides a method of treating cancer comprising administering to a patient in need thereof a therapeutically effective amount of a compound of Formula I-VII.

A variety of cancers may be treated according to the methods of the present invention including, but not limited to: carcinoma of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xeroderma pigmentosum, keratoactanthoma, seminoma, thyroid follicular cancer, and teratocarcinoma. The methods of the invention may also be used to treat accelerated or metastatic cancers of the bladder, pancreatic cancer, prostate cancer, non-small cell lung cancer, colorectal cancer, and breast cancer.

A method of the invention may be administered simultaneously or metronomically with other anti-cancer treatments such as chemotherapy and radiation therapy. The term "simultaneous" or "simultaneously" as used herein, means that the other anti-cancer treatment and the compound of the present invention are administered within 48 hours, preferably 24 hours, more preferably 12 hours, yet more preferably 6 hours, and most preferably 3 hours or less, of each other. The term "metronomically" as used herein means the administration of the compounds at times different from the chemotherapy and at a certain frequency relative to repeat administration and/or the chemotherapy regimen.

Chemotherapy treatment may comprise administration of a cytotoxic agent or cytostatic agent, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include but are not limited to the following: alkylating agents (including, without limitation, nitrogen mustards, ethylenimine derivatives, alkyl sulfonates, nitrosoureas and triazenes); uracil mustard, chlormethine, cyclophosphamide (Cytoxan®), ifosfamide, melphalan, chlorambucil, pipobroman, triethylene-melamine, triethylenethiophosphoramine, bisulfan, carmustine, lomustine, streptozocin, dacarbazine, and temozolomide; antimetabolites (including, without limitation, folic acid antagonists, pyrimidine analogs, purine analogs and adenosine deaminase inhibitors); methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins), vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, 1-asparaginase, interferons (preferably IFN-.alpha.), etoposide, and teniposide. Other proliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in J. C. Bulinski et al., J. Cell Sci. 1997, 110, 3055-3064; D. Panda et al., Proc. Natl. Acad. Sci. USA 1997, 94, 10560-10564, P. F. Mühlradt et al., Cancer Res. 1997, 57, 3344-3346; K. C. Nicolaou et al., Nature 1997, 387, 268-272; R. J. Vasquez et al., Mol. Biol. Cell. 1997, 8, 973-985; and D. Panda et al., J. Biol. Chem. 1996, 271, 29807-29812.

Other suitable cytotoxic agents include, but are not limited to, epidophyllotoxin; an antineoplastic enzyme; a topoisomerase inhibitor; procarbazine; mitoxantrone; platinum coordination complexes such as cis-platin and carboplatin, biological response modifiers; growth inhibitors; antihormonal therapeutic agents; leucovorin; tegafur; and haematopoietic growth factors.

Cytostatic agents that may be used according to the methods of the invention include, but are not limited to, hormones and steroids (including synthetic analogs): 17 alpha-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisense, hydroxyprogesterone, aminoglutethimide, estramustine, medroxyprogesteroneacetate, leuprolide, flutamide, toremifene, zoladex. Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and src inhibitors. Also suitable for use as a cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include, but are not limited to, epidermal growth factor inhibitors, Her-2 inhibitors, MEK-1 kinase inhibitors, MAPK kinase inhibitors, PI3 inhibitors, Src kinase inhibitors, and PDGF inhibitors.

The present methods of the invention also encompass treating pancreatitis comprising administering to a patient in need thereof a therapeutically effective amount of a compound or compounds of Formula I-VII. As discussed in I. Gukovsky et al., Gastroenterology 2004, 126, 554-566, key pathologic responses are regulated by PI-3 kinase and may play an important role in pancreatitis.

The present methods also encompass treating ulcers comprising administering to a patient in need thereof a therapeutically effective amount of a compound of Formula I-VII. The present invention also encompasses a method for treating gastric cancer, such as stomach cancer, comprising administering to a patient in need thereof a therapeutically effective amount of a compound of the present invention. As discussed in Bacon et al., Digestive Disease Week Abstract and Itinerary Planner, Vol. 2003, Abstract No. M921 (2003) and Rokutan et al., Digestive Disease Week Abstracts and Itinerary Planner, Vol. 2003, Abstract No. 354 (2003), PI-3 kinase is involved in the adhesion of Helicobacterpylori to gastric cells.

The present invention also encompasses a method for treating age-related macular degeneration (AMD) comprising administering to a patient in need thereof a therapeutically effective amount of a compound of Formula I-VII. As discussed in M. R. Barakat et al., Expert Opin. Investig. Drugs 2009, 18, 637-646, inhibition of VEGF inhibits blood vessel overgrowth associated with AMD. The methods of the invention may also treat AMD by inhibiting angiogenesis.

The methods of the present invention also encompass treating conditions associated with a mutant PTEN comprising administering to a patient in need thereof a therapeutically effective amount of a compound of Formula I-VII. PTEN is a tumor suppressor gene located on chromosome 10q23, in which mutations have been identified in patients with Cowden disease. As discussed in A. Vega et al., J. Invest. Dermatol. 2003, 121, 1356-1359, mutations in PTEN can reduce the ability to inhibit the activation of the proto-oncogene AKT. Inhibitors of PI-3 kinase may inhibit phosphorylation of AKT, thereby reducing the deleterious effect of a mutant PTEN.

Tat is the human immunodeficiency virus type I (HIV-1) trans-activator protein known to be tightly regulated by lysine acetylation (Kiernan et al., EMBO Journal 1999, 18, 6106-6118). It is also known that HIV-1 Tat transcriptional activity is absolutely required for productive HIV viral replication (Jeang, et al., Curr. Top. Microbiol. Immunol. 1994, 188, 123-144). Thus, the interaction of the acetyl-lysine of the Tat protein with one or more bromodomain-containing proteins (which are associated with chromatin remodeling) could mediate gene transcription allowing viral replication. Blocking bromodomain-containing proteins can thus serve to inhibit HIV viral replication and act as a therapeutic treatment for diseases involving HIV viral replication such as AIDS.

The present invention encompasses a method for treating diseases involving HIV viral replication such as, but not limited to, AIDS comprising administering to a patient in need thereof a therapeutically effective amount of a compound of Formula I-VII. The methods of the invention comprise administering one or more compounds of Formula I-VII for treating viral infections such as but not limited to human papillomavirus, Herpesvirus, Epstein-Barr virus, human immunodeficiency virus, hepatis B virus, and hepatitis C virus.

Figure 1B:
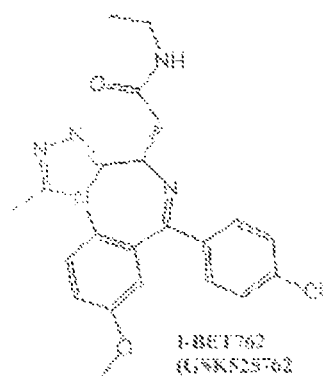
FIG. 1B shows the structure of known BET inhibitor I-BET762.
Figure 1C:
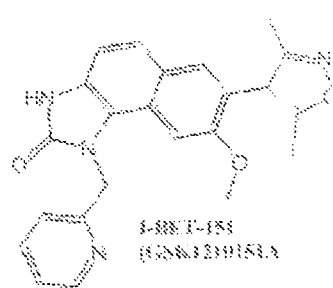
FIG. 1C shows the structure of known BET inhibitor I-BET151.
Figure 1D:
FIG. 1D shows the general structure for acetyl-lysine mimetics acting as bromodomain ligands (4-substituted-3,5-Dimethylisoxazoles).

FIG. 1 shows the structures of several reported BET inhibitors some of which contain the 3,5-dimethylisoxazole chemotype as the acetyl-lysine mimetic moiety (D. S. Hewings, J. Med. Chem. 2011, 54, 6761-6770; D. S. Hewings et al., J. Med. Chem. 2012, 55, 9393-9413; D. S. Hewings et al., J. Med. Chem. 2013, 56, 3217-3227). The earliest inhibitor discovered was JQ1(+) followed by related structures leading to less complex 4-substituted-3,5--dimethyl-isoxazoles (SDMIs) providing a genotype known in the art to participate in Inhibiting BET. In another aspect, the invention provides a method for inhibiting the activity of a bromodomain-containing protein in a patient in need of such treatment comprising administering to said patient one or more compounds of Formula I-VII either alone or in combination with other treatment agents.

In another aspect, the invention provides a method for treating epigenetically-based conditions relating to bromodomain protein activity in a patient in need thereof, comprising administering to said patient a bromodomain-inhibiting compound in Formula I-VII Cellular injury or inflammation triggers a dominant activation of promoter/enhancer elements within the epigenome and drives a pathophysiologic program. Examples of such bromodomain-related disorders include cancer or other proliferative disorder, sepsis, autoimmune diseases, neurological diseases such as Alzheimer's Disease and Huntington's Disease, obesity, type 2 diabetes, atherosclerosis, viral infection, fibrotic diseases, inflammatory diseases, and elements of organ failure syndromes including but not restricted to heart failure following myocardial injury or infarction. Additionally, response to cellular injury in organ failure to include renal, pulmonary, cardiac and brain injury which activates a dominant epigenetic program which propagate the pathophysiologic state and disease are treated using the compounds of Formula I-VII. Bromodomain inhibitors such as compounds of Formula I-VII interfere with and block aberrant transcriptional programs which cause such diseases and hence BET bromodomain inhibitors described in this application may be administered in the treatment of such diseases in humans and other mammals.

The methods of the invention further relate to treating a subject with a MYC-dependent cancer, comprising administration of a compound of Formula I-VII. Subjects with MYC-dependent cancer can be identified and monitored during treatment in any number of ways, for example, by determining MYC mRNA expression levels or MYC protein expression in the tumor. Also, preferred subjects for treatment with the methods of the invention can be identified by historical experience, family history, genetic testing for chromosomal aberrations such as translocations, or known prevalence of MYC activation in certain cancers such as multiple myeloma (J. E. Delmore, Cell, 2011, 146, 904-917), CLL (J. R. Brown et al., Clin. Cancer Res., 2012, 18, 3791-3802), leukaemia (M. A. Dawson, Nature, 2013, 478, 529-533), neuroblastoma (A. Puissant, Cancer Discov. 2013, 3, 308-323), medulloblastoma (Y. J. Cho, J. Clin. Oncol. 2010, 29, 1424-1430).

Diseases and conditions treatable according to the methods of this invention comprise administering one or more compounds of Formula I-VII including, but are not limited to, cancer and other proliferative disorders, sepsis, autoimmune disease, and viral infection. Diseases such as atherosclerosis and type 2 diabetes (V. A. DeWaskin et al., Nature Rev. Drug Disc. 2013, 12, 661-662) and obesity and inflammation (A. C. Belkina et al., Nature Rev. Cancer, 2012, 12, 465-474) are also treatable according to the methods of the invention.

The invention further provides methods for treating or ameliorating cancer or another proliferative disorder by administration of an effective amount of a compound of Formula I-VII to a mammalin including a human in need of such treatment. Examples of cancers treatable using an effective amount of a compound of Formula I-VII include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocyte leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatogenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangio sarcoma, lymphoepithelioma, lymphoma, acute lymphocytic leukemia, acute myelogenous leukemia, chrome lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell turner, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

The methods of this invention further comprise administering one or more compounds of Formula I-VII for treating benign proliferative disorders such as, but not limited to, meningioma, cerebri, seborrheic keratoses, stomach polyps, thyroid nodules, cystic neoplasms of the pancreas, hemangiomas, multiple endocrine neoplasia, nasal polyps, pituitary tumors, juvenile polyposis syndrome, prolactinoma, pseudotumor benign soft tissue tumors, bone tumors, brain and spinal tumors, eyelid and orbital tumors, granuloma, lipoma, vocal cord nodules, polyps, and cysts, chronic pilonidal disease, dermatofibroma, pilar cyst, pyogenic granuloma, and Castleman disease.

The methods of this invention further comprise administering one or more compounds of Formula I-VII for treating infectious and noninfectious inflammatory events and autoimmune and other inflammatory diseases. Examples of autoimmune and inflammatory diseases, disorders, and syndromes treated using the compounds and methods described herein include but are not limited to: appendicitis, pancreatitis, cholecystitis, agammaglobulinemia, psoriasis, allergy, Crohn's disease, irritable bowel syndrome, ulcerative colitis, inflammatory pelvic disease, urethritis, skin sunburn, sinusitis, pneumonitis, encephalitis, meningitis, myocarditis, nephritis, osteomyelitis, myositis, asthma, allergic rhinitis, chronic obstructive pulmonary disease, autoimmune polyglandular disease/syndrome, autoimmune alopecia, pernicious anemia, glomerulonephritis, dermatomyositis, multiple sclerosis, scleroderma, hepatitis, gastritis, enteritis, dermatitis, gingivitis. Sjogren's disease, tissue graft rejection, hyperacute rejection of transplanted organs, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus, rheumatoid arthritis, psoriatic arthritis, juvenile arthritis, osteoarthritis, idiopathic arthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Graves' disease, Guillain-Barre syndrome, Behcet's disease, scleracierna, mycosis fungoides, acute respiratory distress syndrome and ischemia/reperfusion injury. In some embodiments, the present invention provides a method of treating systemic inflammatory response syndromes such as LPS-induced endotoxin shock and/or bacteria-induced sepsis by administration of an effective amount of a compound of Formula I-VII to a mammal in need of such treatment.

G. Administrating and Dosage

A compound or composition of the present invention may be administered in any manner including but not limited to orally, parenterally, sublingually, transdermally, rectally, transmucosally, topically, pulmonarily, nasally, or bucally. Parenteral administration includes but is not limited to intravenous, intraarterial, intraperitoneal, subcutaneous, intramuscular, intrathecal, and intraarticular. A compound(s) or composition of the invention may also be administered via slow controlled i.v. infusion or by release from an implant device.

A therapeutically effective amount of a compound of the invention required for use in therapy varies with the nature of the condition being treated, the length of treatment time desired, the age and the condition of the patient, and is ultimately determined by the attending physician. In general, however, doses employed for adult human treatment typically are in the range of 0.001 mg/kg to about 200 mg/kg per day. The dose may be about 1 µg/kg to about 100 µg/kg per day. The desired dose may be conveniently administered in a single dose, or as multiple doses administered at appropriate intervals, for example as two, three, four or more sub-doses per day. Multiple doses often are desired, or required.

A number of factors may lead to the compounds of the present invention being administered over a wide range of dosages. When given in combination with other therapeutic agents, the dosage of the compounds of the present invention may be given at relatively lower dosages. In addition, the use of targeting agents on a conjugate of the invention is expected to lower the effective dosage required for treatment. As a result, the daily dosage of a compound of the present invention may be from about 1 ng/kg to about 100 mg/kg. The dosage of a compound of the present invention may be at any dosage including, but not limited to, about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

The present invention has multiple aspects, illustrated by the following non-limiting examples. The examples are merely illustrative and do not limit the scope of the invention in anyway.

H. Preparation of Compounds
Synthetic procedure A: Formula II (Z=O).

Synthesis of 7-bromo-2-morpholino-4H-thieno[2,3-e][1,3]oxazin-4-one (2)

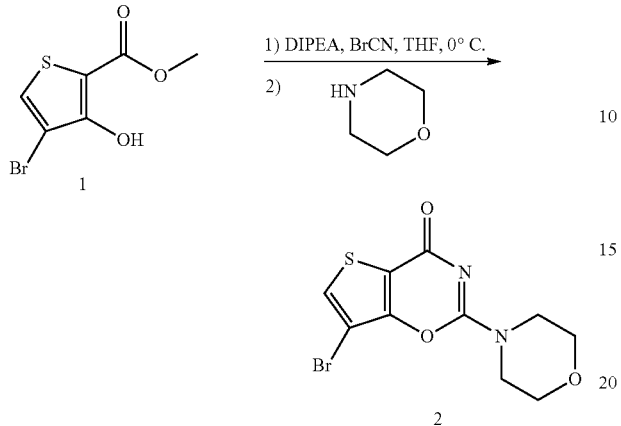

A 40 mL vial was charged with a magnetic stirring bar, THF (10 mL) and, under magnetic stirring conditions, cooled to 0° C. using an ice bath. Then methyl 4-bromo-3-hydroxythiophene-2-carboxylate (1) (1.0 g, 4.22 mmol), cyanogen bromide (223 mg, 2.11 mmol), and N,N-diisopropylethylamine (734 µL, 4.22 mmol) were added to the cooled mixture over 5 minutes. The reaction mixture was allowed to warm to room temperature overnight with continuing stirring. The reaction mixture was then charged with morpholine (387 µL, 3.16 mmol) and stirred overnight. The reaction mixture was then concentrated in vacuo and the residue purified using preparative reverse-phase high-pressure liquid chromatography to give 7-bromo-2-morpholino-4H-thieno[2,3-e][1,3]oxazin-4-one (2) (151 mg, 4.76 mmol).

Synthesis of 2-morpholino-7-phenyl-4H-thieno[2,3-][1,3]oxazin-4-one (3)

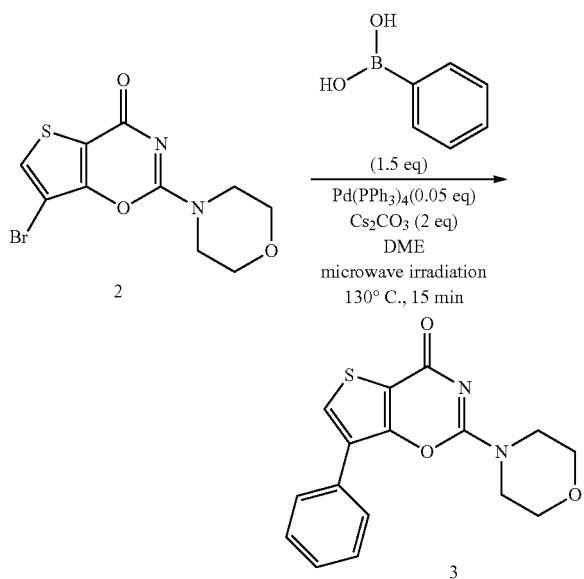

A 2 mL microwave vial was charged with a magnetic stirring bar, 7-bromo-2-morpholino-4H-thieno[2,3-e][1,3]oxazin-4-one (2) (50 mg, 0.16 mmol), phenylboronic acid (29 mg, 0.24 mmol), cesium carbonate (103 mg, 0.32 mmol), tetrakis(triphenylphosphine)palladium(0) (9 mg, 0.008 mmol), and dimethoxyethane (1 mL). The vial was immediately sealed, and the reaction mixture was magnetically stirred and heated via microwave irradiation to 140° C. for 15 minutes. Upon cooling to room temperature, the reaction mixture was concentrated in vacuo and purified using reverse-phase high-pressure liquid chromatography to give 2-morpholino-7-phenyl-4H-thieno[2,3-e][1,3]oxazin-4-one (3).

Synthetic Procedure B. Formula II (Z=NH)

Synthesis of 2-morpholino-7-phenylthieno[3,2-d]pyrimidin-4-(1H)-one (5)

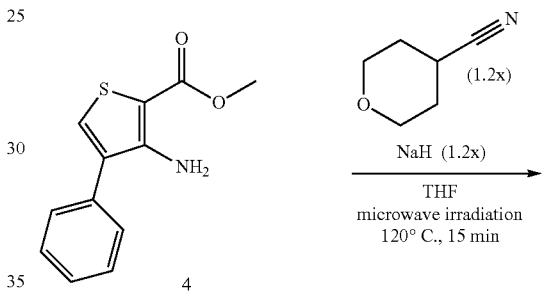

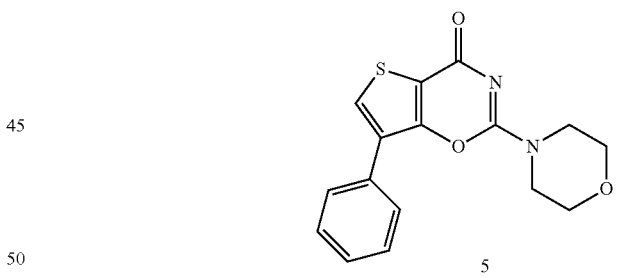

A 2 mL microwave vial was charged with a magnetic stirring bar, methyl 3-amino-4-phenylthiophene-2-carboxylate (4) (50 mg, 0.21 mmol), tetrahydrofuran (1 mL), morpholinocarbonitrile (26 µL, 0.26 mmol) and sodium hydride (10 mg, 0.26 mmol). After the bubbling subsided, the vial was immediately sealed, and the reaction mixture was magnetically stirred and heated via microwave irradiation to 120° C. for 15 minutes. After cooling to room temperature, the reaction was quenched with glacial acetic acid (1 mL), concentrated in vacuo, and purified using reverse-phase high-pressure liquid chromatography to give 2-morpholino-7-phenylthieno[3,2-d]pyrimidin-4(1H)-one (5).

Synthetic Procedure C. Formula III

Synthesis of ethyl 5-amino-1-cyclohexyl-1H-pyrazole-4-carboxylate (7)

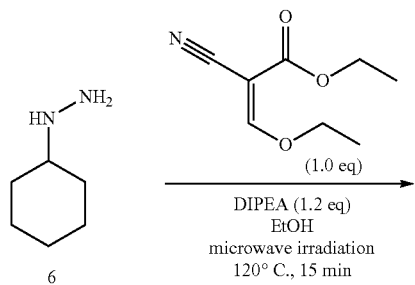

A 2 mL microwave vial was charged with a magnetic stirring bar, cyclohexylhydrazine (6) (200 mg, 1.75 mmol), ethyl 2-cyano-3-ethoxyacrylate (302 mg, 1.79 mmol), ethanol (1.5 mL) and N,N-diisopropylethylamine (335 μL, 1.93 mmol). The vial was immediately sealed, and the reaction mixture was magnetically stirred and heated via microwave irradiation to 120° C. for 15 minutes. After cooling to room temperature, the reaction mixture was diluted with water (approximately 5 mL) forming a yellow oil. Upon manually stirring, a precipitate was formed, filtered and dried to give ethyl 5-amino-1-cyclohexyl-1H-pyrazole-4--carboxylate (7) (247 mg, 1.04 mmol).

Synthesis of 1-cyclohexyl-6-morpholino-1H-pyrazolo[3,4-d]pyrimidin-4(7H)-one (8)

A 2 mL microwave vial was charged with a magnetic stirring bar, ethyl 5-amino-1-cyclohexyl-1H-pyrazole-4--carboxylate (7) (100 mg, 0.42 mmol), tetrahydrofuran (1 mL), 4-morpholinecarbonitrile (60 μL, 0.59 mmol), and sodium hydride (20 mg, 0.50 mmol). After the bubbling subsided, the vial was immediately sealed, and the reaction mixture was magnetically stirred and heated via microwave irradiation to 130° C. for 15 minutes. After cooling to room temperature the reaction mixture was charged with 10% hydrochloric acid in water (1 mL) forming a precipitate. The precipitate was filtered and dried to give 1-cyclohexyl-6-morpholino-1H-pyrazolo[3,4-d]pyrimidin-4(7H)-one (8) (92 mg, 0.30 mmol).

Synthetic Procedure D. Formula IV

Synthesis of ethyl 2-cyano-2-(1-ethoxyethylideneamino)acetate (10)

A 40 mL vial was charged with a magnetic stirring bar, ethyl 2-amino-2-cyanoacetate (9) (2.0 g, 15.61 mmol), and triethyl orthoacetate (10 mL). The reaction solution was magnetically stirred and heated to 100° C. overnight. The solvent was then removed in vacuo to give ethyl 2-cyano-2-(1-ethoxyethylideneamino)acetate (10) (3.20 g, 16.14 mmol) as a yellow oil, which was used without any further purification.

Synthesis of 8-methyl-2-morpholino-9-phenyl-3H-purin-6(9H)-one (11)

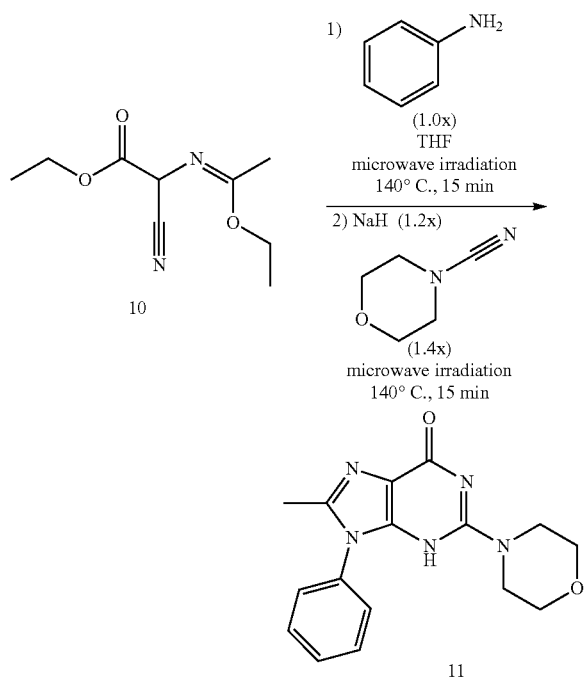

A 5 mL microwave vial was charged with a magnetic stirring bar, ethyl 2-cyano-2-(1-ethoxyethylideneamino)acetate (10) (100 mg, 0.50 mmol), tetrahydrofuran (2 mL), and aniline (46 μL, 0.50 mmol). The reaction solution was magnetically stirred, and heated in a microwave reactor for 25 minutes to 140° C. After cooling to room temperature, the reaction was charged with morpholinocarbonitrile (72 μL, 0.71 mmol) and sodium hydride (24 mg, 0.60 mmol). After the bubbling subsided, the reaction solution was magnetically stirred and heated in a microwave reactor for 15 minutes to 140° C. After cooling to room temperature, the reaction was quenched with glacial acetic acid (1 mL), concentrated in vacuo, and purified using reverse-phase high-pressure liquid chromatography to give 8-methyl-2-morpholino-9-phenyl-3H-purin-6(9H)-one (11).

Synthetic procedure E: Formula V (Z=O).

Synthesis of 7-bromo-2-thiomorpholino-4H-thieno[2,3-e][1,3]oxazin-4-one (13)

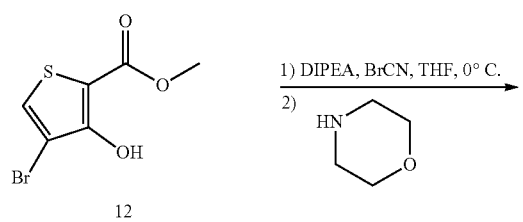

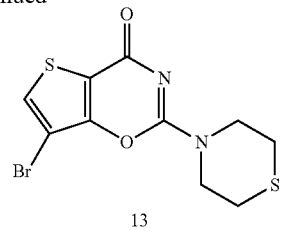

A 40 mL vial is charged with a magnetic stirring bar, THF (10 mL) and, under magnetic stirring conditions, is cooled to 0° C. using an ice bath. Methyl 4-bromo-3-hydroxythiophene-2--carboxylate (12) (1.0 g, 4.22 mmol), cyanogen bromide (223 mg, 2.11 mmol), and N,N-diisopropylethylamine (734 μL, 4.22 mmol) each is added to the cooled mixture over 5 minutes. The reaction mixture is allowed to warm to room temperature overnight with continuing stirring. The reaction mixture is charged with thiomorpholine (326 mg, 3.16 mmol) and stirred overnight. The reaction mixture is concentrated in vacuo and the residue is purified using preparative reverse-phase high-pressure liquid chromatography to give 7-bromo-2-thiomorpholino-4H-thieno[2,3-e][1,3]oxazin-4-one (13).

Synthesis of 2-thiomorpholino-7-phenyl-4H-thieno[2,3-e][1,3]oxazin-4-one (14)

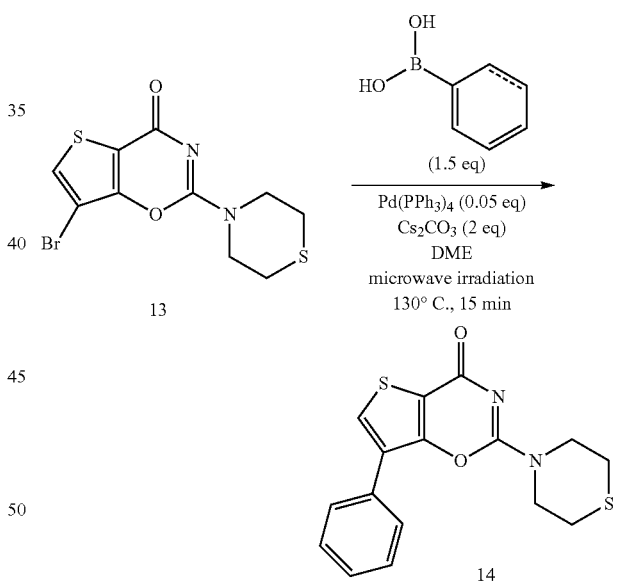

A 2 mL microwave vial is charged with a magnetic stirring bar, 7-bromo-2-thiomorpholino-4H-thieno[2,3-e][1,3]oxazin-4--one (13) (0.16 mmol), phenylboronic acid (29 mg, 0.24 mmol), cesium carbonate (103 mg, 0.32 mmol), tetrakis(triphenylphosphine)palladium(0) (9 mg, 0.008 mmol), and dimethoxyethane (1 mL). The vial is immediately sealed, and the reaction mixture is magnetically stirred and is heated via microwave irradiation to 140° C. for 15 minutes. Upon cooling to room temperature, the reaction mixture is concentrated in vacuo and is purified using reverse-phase high-pressure liquid chromatography to give 2-thiomorpholino-7-phenyl-4H-thieno[2,3-e][1,3]oxazin-4-one (14).

Synthetic Procedure F. Formula V (Z=NH)

Synthesis of 2-thiomorpholino-7-phenylthieno[3,2-d]pyrimidin-4(1H)-one (16)

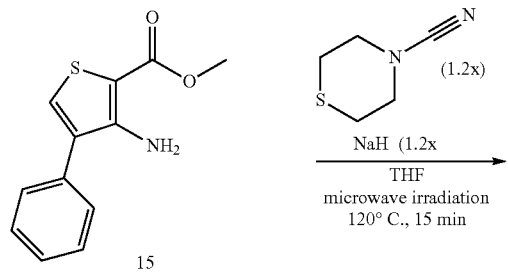

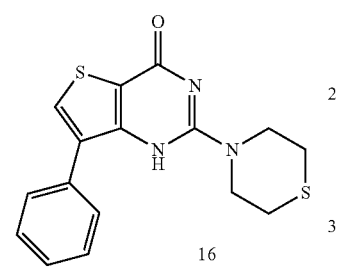

A 2 mL microwave vial is charged with a magnetic stirring bar, methyl 3-amino-4-phenylthiophene-2-carboxylate (15) (0.21 mmol), tetrahydrofuran (1 mL), thiomorpholinocarbonitrile (33.3 mg, 0.26 mmol) and sodium hydride (10 mg, 0.26 mmol). After the bubbling subsides, the vial is immediately sealed, and the reaction mixture is magnetically stirred and is heated via microwave irradiation to 120° C. for 15 minutes. After cooling to room temperature, the reaction is quenched with glacial acetic acid (1 mL), concentrated in vacuo, and is purified using reverse-phase high-pressure liquid chromatography to give 2-thiomorpholino-7-phenylthieno[3,2-d]pyrimidin-4(1H)-one (16).

Synthetic Procedure G. Formula VI (Z=NH)

Synthesis of 1-cyclohexyl-6-morpholino-1H-pyrazolo[3,4-d]pyrimidin-4(7H)-one (17)

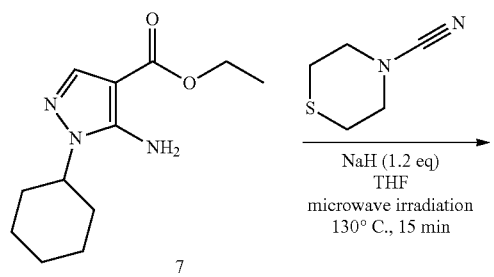

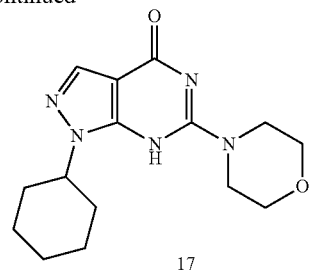

A 2 mL microwave vial is charged with a magnetic stirring bar, ethyl 5-amino-1-cyclohexyl-1H-pyrazole-4-carboxylate (7) (100 mg, 0.42 mmol), tetrahydrofuran (1 mL), 4-thiomorpholinecarbonitrile (85.6 mg, 0.59 mmol), and sodium hydride (20 mg, 0.50 mmol). After the bubbling subsided, the vial is immediately sealed, and the reaction mixture is magnetically stirred and is heated via microwave irradiation to 130° C. for 15 minutes. After cooling to room temperature the reaction mixture is charged with 10% hydrochloric acid in water (1 mL). The precipitate is filtered and is dried to give 1-cyclohexyl-6-morpholino-1H-pyrazolo[3,4-d]pyrimidin-4(7H)-one (17).

Synthetic Procedure H. Formula VII

Synthesis of 8-methyl-2-thiomorpholino-9-phenyl-3H-purin-6(9H)-one (18)

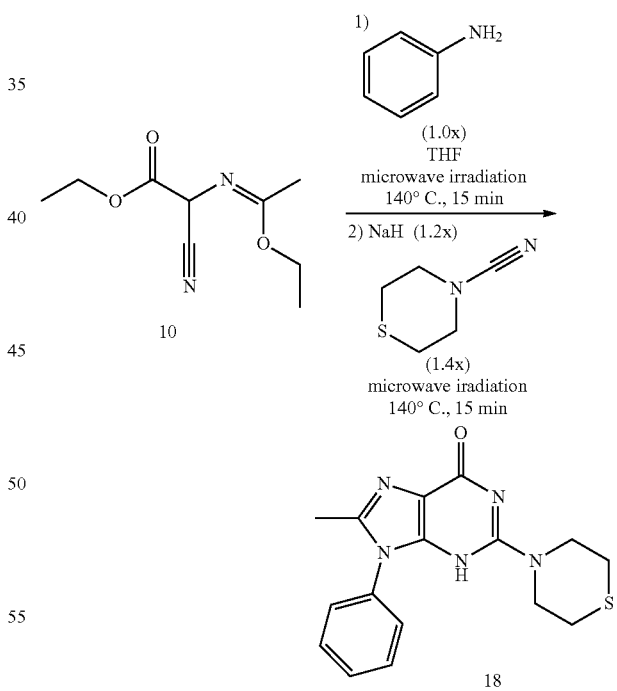

A 5 mL microwave vial is charged with a magnetic stirring bar, ethyl 2-cyano-2-(1-ethoxyethylideneamino)acetate (10) (100 mg, 0.50 mmol), tetrahydrofuran (2 mL), and aniline (46 µL, 0.50 mmol). The reaction solution is magnetically stirred and is heated in a microwave reactor for 25 minutes to 140° C. After cooling to room temperature, the reaction vial is charged with thiomorpholinocarbonitrile (91 mg, 0.71 mmol) and sodium hydride (24 mg, 0.60 mmol).

After the bubbling subsided, the reaction solution is magnetically stirred and is heated in a microwave reactor for 15 minutes to 140° C. After cooling to room temperature, the reaction is quenched with glacial acetic acid (1 mL), is concentrated in vacuo, and is purified using reverse-phase high-pressure liquid chromatography to give 8-methyl-2-thiomorpholino-9-phenyl-3H-purin-6(9H)-one (18).

Synthetic Procedure I. Formula VI (Z=O)

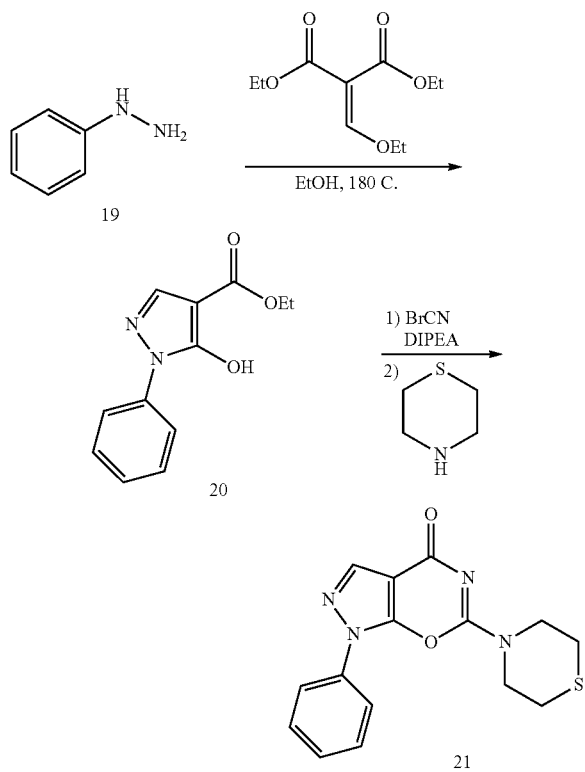

A 5 mL microwave vial is charged with a magnetic stirring bar and a solution of diethyl ethoxymethylenemalonate (0.25 mmol) in 2 mL of absolute ethanol. A 0.25 mmol portion of phenyl hydrazine is added to the vial. The vial is sealed and is magnetically stirred and is heated in a microwave reactor for 25 minutes to 180° C. After cooling to room temperature, the reaction mixture is removed and purified by column chromatography (silica gel or reverse phase HPLC) to yield >85% pure compound 20. A 5 mL vial is charged with a magnetic stirring bar, THF (2 mL) and, under magnetic stirring conditions, is cooled to 0° C. using an ice bath. A 0.422 mmol portion of compound 20 and methyl cyanogen bromide (223 mg, 0.2 mmol), and N,N-diisopropylethylamine (73 μL, 0.422 mmol) is added to the cooled mixture over a 5 minute period. The reaction mixture is allowed to warm to room temperature overnight with continuing stirring. The reaction mixture is charged with thiomorpholine (32.6 mg, 0.316 mmol) and stirred overnight. The reaction mixture is concentrated in vacuo and the residue is purified using preparative reverse-phase high-pressure liquid chromatography to give compound 21.

As described by the non-limiting list of amines and cyanoamines in section D.1. above it will be appreciated that the above representative synthesis of compounds using morpholine or cyano-morpholine can be utilized in identical fashion with a variety of amines and cyanoamines. Additionally, the compounds of Formula I-VII containing the chromone carbonyl (M=O) may be converted to the thione analog (M=O) by exposure to Lawasson's reagent using conditions described by G. Morales, J. Med. Chem. 2013, 56, 1922-1939 and Example 3.

Representative compounds of the invention are depicted in Tables 1-4 and 6-10 as merely illustrative and not limiting of the scope of the invention in any way.

EXAMPLE 1

Biological Testing of Compounds

Representative compounds of the invention were tested for inhibitory activity, which is summarized in Table 5. Data provide the inhibitory concentration needed to inhibit 50% of the enzymatic activity ($IC_{50}$) for PI3K (alpha, beta, delta, and gamma isoforms), mTOR, PLK-1, PIM-1 and DNA-PK and the percent enzyme inhibition at certain concentrations of tested compound (columns 2-24). The assays determined the amount of radioactive phosphate transferred from P-33 labelled ATP to the substrate by the enzyme in the presence of various concentrations of the inhibitor test compounds. The concentration needed to inhibit 50% of the pAKT signal (column 25 of Table 5) was determined as follows: PC3 cells were obtained from the American Type Culture Collection (ATCC, Manassas, Va., Cat.#CRL-1435). Two million cells from the prostate cancer line PC3 were placed into 6 cm culture dishes and allowed to grow in complete RPMI 1640 media (Invitrogen, Carlsbad, Calif., Cat.#22400-105) with 10% fetal bovine serum (Invitrogen, Carlsbad, Calif., Cat.#10438-026). After this time period the cells were serum starved for 5 hours followed by application of the test compound. Test compound was added as a DMSO (dimethyl sulfoxide) solution such that the final DMSO concentration in the cell media was less than or equal to 0.2% by volume. After 30 minutes of exposure the growth factor stimulant, human IGF-1 (Pepro Tech, Inc., Rocky Hill, N.J., Cat.#100-11), was added in each well. After 30 minutes of IGF-1 exposure, cells were removed from the media and cell lysates were prepared using RIPA Lysis buffer (Upstate, Lake Placid, N.Y., Cat.#20-188), keeping on ice. The pAKT serine 473 level was measured in duplicate samples of the cell lysates using commercially available assays such as the Pathscan® Sandwich ELIAS kit for Ser473 pAKT (Cell Signaling, Danvers, Mass., Cat.#7160). A SpectraMax Plus spectrophotometric plate reader (Molecular Devices, Sunnydale, Calif.) was used to measure the optical density signal for pAKT at 450 nm (OD450 nm). The pAKT OD450 nm readings were normalized by total protein amount in the cell lysates determined by standard methods. Concentrations of test compounds required to inhibit IGF stimulated pAKT levels to 50% of maximum levels in PC3 cells (termed $DM_{50}$ for decreased maximum 50%) were calculated by inputting the dose responses in the software package GraphPad Prism4 (GraphPad Software, Inc., San Diego, Calif.).

The PC3 cell proliferation data in column 26 of Table 5 was obtained as follows: PC3 cells were obtained from the American Type Culture Collection (ATCC, Manassas, Va., Cat.#CRL-1435). Two thousand cells from the prostate cancer line PC3 were placed in 50 μL of complete RPMI 1640 media (Invitrogen, Carlsbad, Calif., Cat.#22400-105) with 10% fetal bovine serum, (Invitrogen, Carlsbad, Calif., Cat.#10438-026) into each well of 96-well cell culture plates in a hexaplicate sampling pattern. A 50 μL aliquot of test compound (prepared from stock test compounds in DMSO diluted into media) was added to the appropriate well such that the final concentrations of test compound were 200, 40, 8, 1.6, 0.32, 0.064, 0.0128, 0.00256, and 0 µM and the final DMSO concentration was less than or equal to 0.2%. The plates were incubated for 72 hours 37° C. in an atmosphere of 5% $CO_2$. At the end of this time a 10 µL aliquot of WST solution (Roche Applied Science, Mannheim, Germany) was added into each of the wells. Cells were exposed to the WST solution for 4 hours. A SpectraMax Plus spectrophotometric plate reader (Molecular Devices, Sunnydale, Calif.) was then used to measure the optical density at 450 nm (OD450 nm). Sigmoidal curves were drawn for the dose responses and $IC_{50}$ values were calculated using the software package GraphPad Prism4 (GraphPad Software, Inc., San Diego, Calif.).

EXAMPLE 2

BRD4 Molecular Modeling Testing of Compounds

BRD4 Binding Value Column in Tables 1-10; Modeling Results Demonstrating Compounds of Formula II-VII Bind the Acetyl-Lysine Region Computational modeling was performed using the readily available AutoDock (http://autodock.scripps.edu/ and http://vina.scripps.edu/) suite of software tools. AutoDock Vina was used to dock in silico the compounds of the invention (Formulas I-VII) at the site where the LY294002 compound has been described to reside in BRD4-BD1 (bromodomain 1 of BRD4) which has been described in the crystal structure (A. Dittmann et al., 2014, 9(2), 495-502). As proof of concept, we docked LY294002 at the same BRD4-BD1 binding site found in the crystal structure of LY294002/BRD4(BR1) and confirmed that the docked LY294002 conformation overlays almost perfectly with the co-crystallized LY294002. The docking results of the compounds of the invention with the empty crystal structure of BRD4 (co-crystallized LY294002 removed) are shown (along with structures of the compounds of the invention) with the docking score (binding energy) given as delta-G (enthalpy, kcal/mol). It should be noted that the more negative the number or value of the docking score is, the stronger is the predicted binding energy at the BRD4 site that recognizes the acetyl lysine of chromatin. We assayed CAL101, a known PI3K inhibitor (selective for the delta isoform) and the only FDA-approved PI3K inhibitor, and showed no significant BRD4 inhibition (>50,000 nM). The in silico model showed that CAL101 could not bind to the BRD4-BD1 acetyl-lysine site confirming the observed assay results providing further support for the value of the in silico model for predicting binding potentials of the compounds of the invention with the BRD4 protein structure. It should be noted that in this model LY294002 gives a binding value of −9.66. In Tables 1-4 and 6-10, a value of 0 (zero) means none of the top-ten best predicted binding poses for a compound could bind at the BRD4 acetyl-lysine recognition cavity with the established binding conformation. An entry of N/A indicates that no molecular modeling was performed and, consequently, there is no available data to include in the table. Taken together, the results of Table 5 (PI3K inhibition) with the BRD4 binding data (Tables 1-4 and 6-10) demonstrate that compounds of Formula I-VII are inhibitors of PI3K, or inhibitors of bromodomains (illustrated by BRD4 inhibition), or dual inhibitors of both PI3K and bromodomains such as BRD4.

EXAMPLE 3

Conversion of Compounds from Carbonyl (M=O) to Thiocarbonyl (Thione, M=S)

A 2 mL conical microwave vial is charged with a magnetic stirring bar, 488 µmol of carbonyl containing compound of Formula I-VII (M=O), Lawesson's reagent (118 mg, 293 µmol), and toluene (2 mL). The reaction mixture is sealed, and the reaction mixture is magnetically stirred and is heated via microwave irradiation at 130° C. for 20 min. The final mixture is poured onto water (approximately 30 mL) and is extracted with dichloromethane (3×5 mL). The combined extracts is dried over anhydrous magnesium sulfate, is filtered, and is concentrated to dryness. The crude reaction mixture is then purified via column chromatography. Elution of the silica gel column is performed with a mix of hexanes/ethyl acetate (1:1). Elution is continued with 100% ethyl acetate to afforded pure thione (Formula I-VII, M=S).

TABLE 1

Illustrative compounds of Formula II (Z=O).

| Compound Number | Structure | Mass Expected | Mass Found | Synthetic Method | BRD4 Binding Score |
|---|---|---|---|---|---|
| 3 | 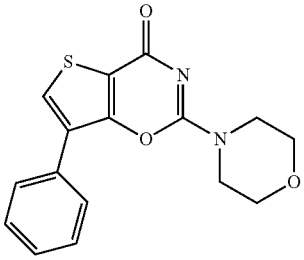 [SMILES: O=c1nc(N2CCOCC2)oc2c(-c3ccccc3)csc12] | 314 | 315 (M + H) | A | −8.13 |

TABLE 1-continued
Illustrative compounds of Formula II (Z=O).
| Compound Number | Structure | Mass Expected | Mass Found | Synthetic Method | BRD4 Binding Score |
|---|---|---|---|---|---|
| 12 | 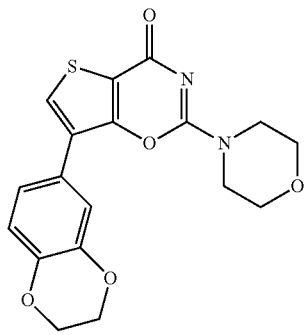 [SMILES: O=c1nc(N2CCOCC2)oc2c(-c3ccc4c(c3)OCCO4)csc12] | 372 | 373 (M + H) | A | −8.53 |
| 13 | 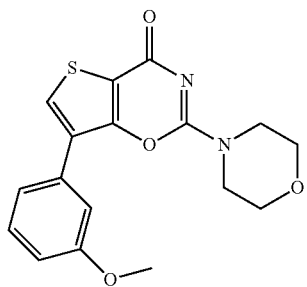 [SMILES: COc1cccc(-c2csc3c(=O)nc(N4CCOCC4)oc23)c1] | 344 | 345 (M + H) | A | −7.65 |
| 14 | 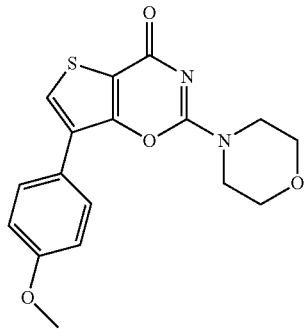 [SMILES: COc1ccc(-c2csc3c(=O)nc(N4CCOCC4)oc23)cc1] | 344 | 345 (M + H) | A | −7.81 |
| 15 | 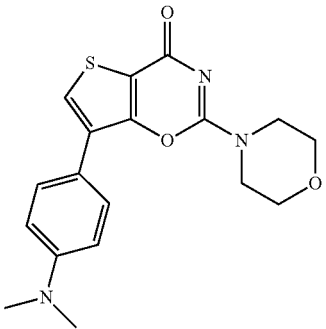 [SMILES: CN(C)c1ccc(-c2csc3c(=O)nc(N4CCOCC4)oc23)cc1] | 357 | 358 (M + H) | A | −7.87 |

TABLE 1-continued

Illustrative compounds of Formula II (Z=O).

| Compound Number | Structure | Mass Expected | Mass Found | Synthetic Method | BRD4 Binding Score |
|---|---|---|---|---|---|
| 16 | 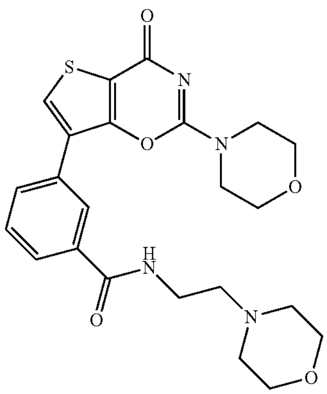 [SMILES: O=C(NCCN1CCOCC1)c1cccc(-c2csc3c(=O)nc(N4CCOCC4)oc23)c1] | 470 | 471 (M + H) | A | −8.01 |
| 17 | 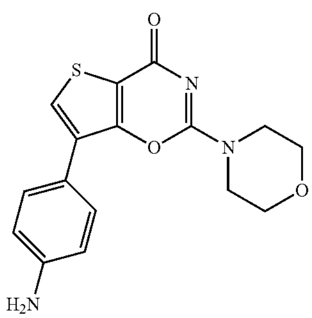 [SMILES: Nc1ccc(-c2csc3c(=O)nc(N4CCOCC4)oc23)cc1] | 329 | 330 (M + H) | A | −7.67 |
| 18 | 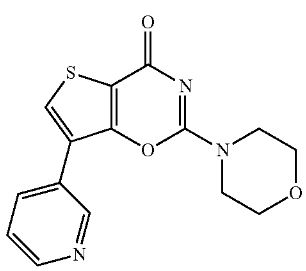 [SMILES: O=c1nc(N2CCOCC2)oc2c(-c3cccnc3)csc12] | 315 | 316 (M + H) | A | −7.62 |
| 19 | 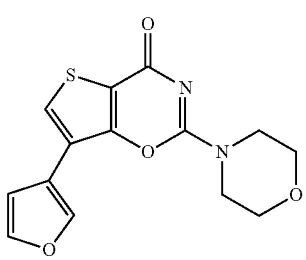 [SMILES: O=c1nc(N2CCOCC2)oc2c(-c3ccoc3)csc12] | 304 | 305 (M + H) | A | −7.20 |

TABLE 1-continued

Illustrative compounds of Formula II (Z=O).

| Compound Number | Structure | Mass Expected | Mass Found | Synthetic Method | BRD4 Binding Score |
|---|---|---|---|---|---|
| 20 | 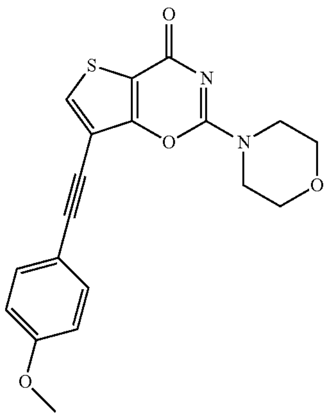 [SMILES: COc1ccc(C#Cc2csc3c(=O)nc(N4CCOCC4)oc23)cc1] | 368 | 369 (M + H) | A | −7.62 |
| 2 | 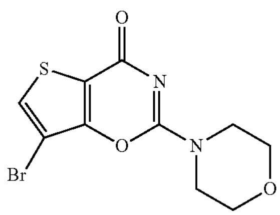 [SMILES: O=c1nc(N2CCOCC2)oc2c(Br)csc12] | 317 | 318 (M + H) | A | N/A |

TABLE 2

Illustrative compounds of formula II (Z=NR3)

| Compound Number | Structure | Mass Expected | Mass Found | Synthetic Method | BRD Binding Score |
|---|---|---|---|---|---|
| 5 | 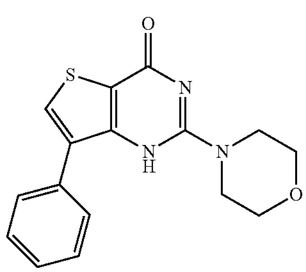 [SMILES: O=c1nc(N2CCOCC2)[nH]c2c(-c3ccccc3)csc12] | 313 | 314 (M + H) | B | −7.85 |
| 21 | 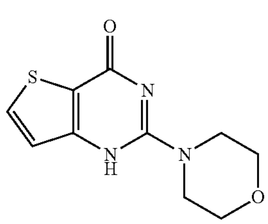 [SMILES: O=c1nc(N2CCOCC2)[nH]c2ccsc12] | 237 | 238 (M + H) | B | N/A |

TABLE 3

Illustrative compounds of formula III (Z=NR3)

| Compound Number | Structure | Mass Expected | Mass Found | Synthetic Method | BRD Binding Score |
|---|---|---|---|---|---|
| 8 | 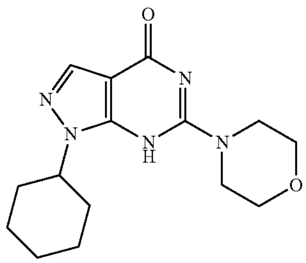 [SMILES: O=c1nc(N2CCOCC2)[nH]c2c1cnn2C1CCCCC1] | 303 | 304 (M + H) | C | −7.44 |
| 22 | 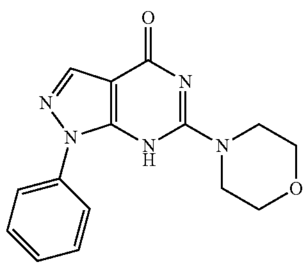 [SMILES: O=c1nc(N2CCOCC2)[nH]c2c1cnn2-c1ccccc1] | 297 | 298 (M + H) | C | −8.40 |
| 23 | 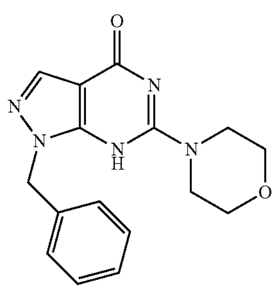 [SMILES: O=c1nc(N2CCOCC2)[nH]c2c1cnn2Cc1ccccc1] | 311 | 312 (M + H) | C | 0.00 |
| 24 | 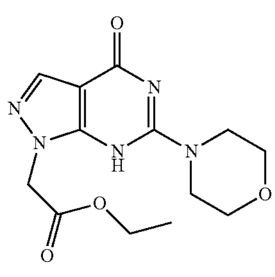 [SMILES: CCOC(=O)Cn1ncc2c(=O)nc(N3CCOCC3)[nH]c21] | 307 | 308 | C | −6.68 |
| 25 | 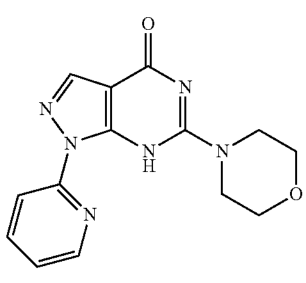 [SMILES: O=c1nc(N2CCOCC2)[nH]c2c1cnn2-c1ccccn1] | 298 | 299 | C | −7.26 |

TABLE 3-continued

Illustrative compounds of formula III (Z=NR3)

| Compound Number | Structure | Mass Expected | Mass Found | Synthetic Method | BRD Binding Score |
|---|---|---|---|---|---|
| 26 | 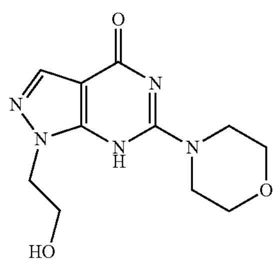 [SMILES: O=c1nc(N2CCOCC2)[nH]c2c1cnn2CCO] | 265 | 266 (M + H) | C | −6.45 |
| 27 | 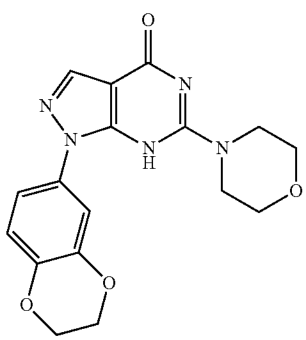 [SMILES: O=c1nc(N2CCOCC2)[nH]c2c1cnn2-c1ccc2c(c1)OCCO2] | 355 | 356 (M + H) | C | −7.84 |
| 28 | 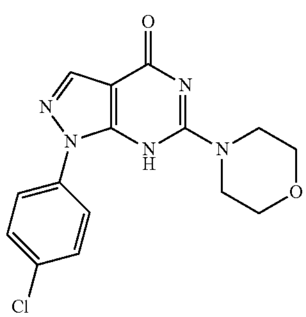 [SMILES: O=c1nc(N2CCOCC2)[nH]c2c1cnn2-c1ccc(Cl)cc1] | 331 | 332 (M + H) | C | −7.24 |

TABLE 4

Illustrative compounds of formula IV

| Compound Number | Structure | Mass Expected | Mass Found | Synthetic Method | BRD Binding Score |
|---|---|---|---|---|---|
| 11 | 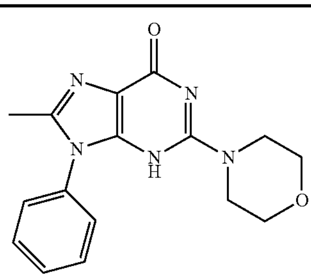 | 311 | 312 (M + H) | D | −7.45 |

TABLE 4-continued
Illustrative compounds of formula IV
| Compound Number | Structure | Mass Expected | Mass Found | Synthetic Method | BRD Binding Score |
|---|---|---|---|---|---|
| 29 | 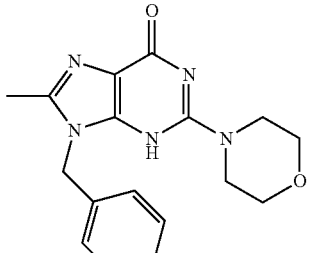 | 325 | 326 (M + H) | D | 0.0 |
| 30 | 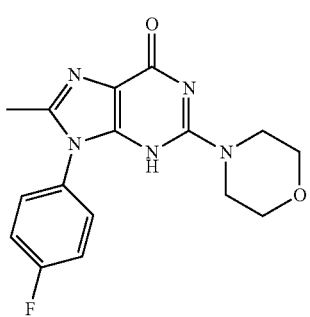 [SMILES: Cc1nc2c(=O)nc(N3CCOCC3)[nH]c2n1-c1ccc(F)cc1] | 329 | 330 (M + H) | D | −6.85 |
| 31 | 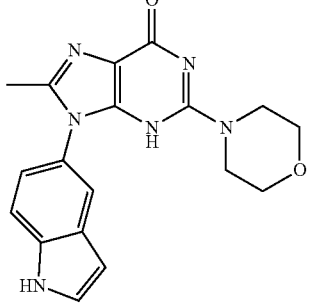 | 350 | 351 (M + H) | D | 0.0 |
| 32 | 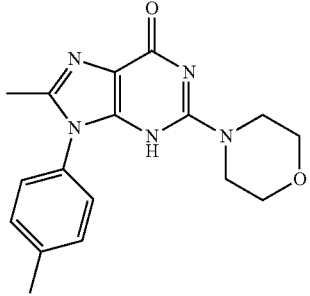 [SMILES: Cc1ccc(-n2c(C)nc3c(=O)nc(N4CCOCC4)[nH]c32)cc1] | 325 | 326 (M + H) | D | 0.0 |
TABLE 5
Biological data of illustrative compounds.
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|
| 3 | 1.4 | 10 | 1.5 | 5.5 |  | 2.3 |  |  |  |  |  |  | 4 |  |  |  |  |  |  |  |  |  |  | 11 | 28 |
| 12 |  |  |  |  |  |  |  |  |  | 53 |  | 72 | 0 | 0 |  |  |  |  |  |  |  |  |  |  | 4.7 |

TABLE 5-continued

Biological data of illustrative compounds.

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|----|----|----|----|----|----|----|----|----|----|----|----|----|----|----|----|----|
| 13 | | | | | | | | | 6.8 | | 0 | | 0 | 0 | | | | | | | | | | | 94 |
| 14 | | | | | | | | | 19 | | 27 | | 0 | 0 | | | | | | | | | | | |
| 15 | | | | | | | | | 11 | | 33 | | 0 | 0 | | | | | | | | | | | 20 |
| 16 | | | | | | | | | 16 | | 17 | | 0 | 0 | | | | | | | | | | | 31 |
| 17 | | | | | | | | | 22 | | 32 | | 0 | 0 | | | | | | | | | | | 108 |
| 18 | | | | | | | | | 0 | | 0 | | 0 | 0 | | | | | | | | | | | |
| 19 | | | | | | | | | 15 | | 0 | | 3 | 0 | | | | | | | | | | | |
| 20 | | | | | | | | | 0 | | 0 | | 0 | 0 | | | | | | | | | | | |
| 2 | | | | | | | | | | | | | | | | | | | | | | | | | |
| 5 | | | | | | | | | | | | | | | | | | 12 | | | | | | | 246 |
| 21 | | | | | | | | | | | | | | | | | | | | | | | | | |
| 8 | | | | | | | | 24 | 2 | | | | | | | | | 9.2 | 18 | 4.8 | 11 | 3.4 | 3.2 | | |
| 22 | | | | | | | | | 14 | | | | 42 | | | | | | 20 | 8 | | | 45 | | 263 |
| 23 | | | | | | | | 24 | 6.6 | | | | | | | | | 14 | 0 | 15 | 0 | 4.9 | 2.1 | | |
| 24 | | | | | | | | 24 | 6.6 | | | | | | | | | 22 | 7.2 | 14 | 0 | 7.5 | 0.9 | | 1.4 |
| 25 | | | | | | | | 24 | 6.6 | | | | | | | | | 4.7 | 10 | 35 | 0 | 2.6 | 9.4 | | |
| 26 | | | | | | | | 24 | 9 | | | | | | | | | 14 | 26 | 0.6 | 0.5 | 3.3 | 1.5 | | |
| 27 | | | | | | | 1 | 24 | 30 | | | | | | | | | 12 | 50 | 48 | 4.4 | | | | 149 |
| 28 | | | | | | | | | 6.9 | | | | | | | | | | 0 | | | | | | |
| 11 | | | | | | | | | 2.6 | 0 | 32 | 0 | 0 | 0 | 0 | 0 | | | | | | | | | |
| 29 | | | | | | | | | 7 | 0 | 0 | 0 | 0 | 0 | 0 | 0 | | | | | | | | | |
| 30 | | | | | | | | | 4.7 | 14 | 32 | 3 | 0 | 0 | 0 | 0 | | | | | | | | | |
| 31 | | | | | | | | | 7.5 | 2.5 | 8.7 | 7.5 | 0 | 0 | 0 | 0 | | | | | | | | | |
| 32 | | | | | | | | | 0 | 0 | 15 | 1 | 0 | 0 | 0 | 0 | | | | | | | | | |

Table 5. Column Number Key
1. Cpd No,
2. PI3K-alpha(IC$_{50}$ in μM),
3. PI3K-beta(IC$_{50}$ in μM),
4. PI3K-delta (IC$_{50}$ in μM),
5. PI3K-gamma (IC$_{50}$ in μM),
6. mTOR (IC$_{50}$ in μM),
7. PLK-1 (IC$_{50}$ in μM),
8. PIM-1(IC$_{50}$ in μM),
9. DNA-PK(IC$_{50}$ in μM),
10. PI3K-alpha (% Inh at 300 nM),
11. PI3K-beta(% Inh at 300 nM),
12. PI3K-delta(% Inh at 300 nM),
13. PI3K-gamma(% Inh at 300 nM),
14. mTOR(% Inh at 300 nM),
15. PLK-1(% Inh at 300 nM),
16. PIM-1(% Inh at 300 nM),
17. DNA-PK(% Inh at 300 nM),
18. PI3K-alpha(% Inh at 10 μM),
19. PI3K-beta(% Inh at 10 μM),
20. PI3K-delta(% Inh at 10 μM),
21. PI3K-gamma(% Inh at 10 μM),
22. mTOR(% Inh at 10 μM),
23. PLK-1(% Inh at 10 μM),
24. PIM-1(% Inh at 10 μM),
25. PC3 pAKT(IC$_{50}$ μM),
26. PC3 cell proliferation(IC$_{50}$ μM)

TABLE 6

Formula V: Z=O

| Compound Number | Structure | Mass Expected | BRD4 Binding Score | Synthetic Method |
|---|---|---|---|---|
| 33 | (structure: phenyl-substituted thieno[3,2-d][1,3]oxazin-4-one with thiomorpholine at position 2) | 330.42 | −7.74 | E |

TABLE 6-continued

| | Formula V: Z=O | | | |
|---|---|---|---|---|
| Compound Number | Structure | Mass Expected | BRD4 Binding Score | Synthetic Method |
| 34 | | 313.37 | −8.07 | E |
| 35 | | 312.39 | −7.79 | E |
| 36 | | 327.40 | −7.67 | E |
| 37 | | 298.36 | −8.19 | E |
| 38 | | 328.39 | −8.08 | E |

TABLE 6-continued

| Formula V: Z=O | | | | |
|---|---|---|---|---|
| Compound Number | Structure | Mass Expected | BRD4 Binding Score | Synthetic Method |
| 39 | | 326.37 | −7.94 | E |
| 40 | | 314.32 | −8.41 | E |
| 41 | | 300.33 | −8.02 | E |
| 42 | | 302.35 | −7.59 | E |
| 43 | | 318.41 | −7.07 | E |

TABLE 6-continued
| | Formula V: Z=O | | | |
|---|---|---|---|---|
| Compound Number | Structure | Mass Expected | BRD4 Binding Score | Synthetic Method |
| 44 | 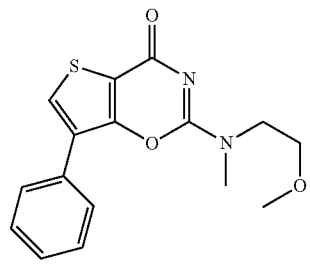 [SMILES: COCCN(C)c1nc(=O)c2scc(-c3ccccc3)c2o1] | 316.38 | −7.15 | E |
| 45 | 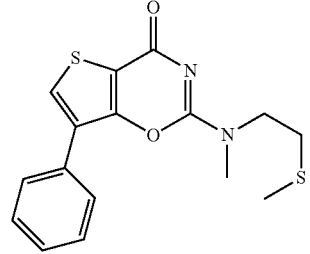 [SMILES: CSCCN(C)c1nc(=O)c2scc(-c3ccccc3)c2o1] | 332.44 | −7.09 | E |
| 46 | 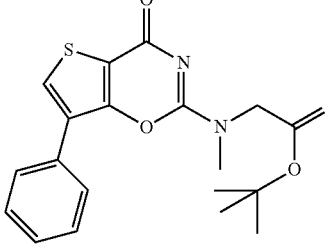 | 372.44 | −7.02 | E |
TABLE 7
| | Formula V: Z=NH | | | |
|---|---|---|---|---|
| Compound Number | Structure | Mass Expected | BRD4 Binding Score | Synthetic Method |
| 47 | 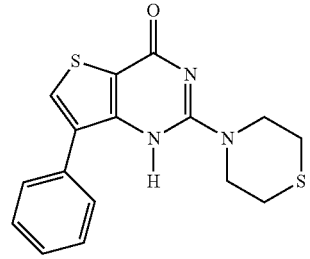 [SMILES: O=c1nc(N2CCSCC2)[nH]c2c(-c3ccccc3)csc12] | 329.44 | −7.92 | F |

TABLE 7-continued

Formula V: Z=NH

| Compound Number | Structure | Mass Expected | BRD4 Binding Score | Synthetic Method |
|---|---|---|---|---|
| 48 | (structure) | 312.39 | −8.32 | F |
| 49 | (structure) | 311.40 | −7.94 | F |
| 50 | (structure) | 326.42 | −7.68 | F |
| 51 | (structure) | 297.38 | −8.11 | F |
| 52 | (structure) | 327.40 | −8.31 | F |

TABLE 7-continued

| | Formula V: Z=NH | | | |
|---|---|---|---|---|
| Compound Number | Structure | Mass Expected | BRD4 Binding Score | Synthetic Method |
| 53 | | 325.39 | −8.24 | F |
| 54 | | 313.33 | −8.30 | F |
| 55 | | 299.35 | −7.96 | F |
| 56 | | 301.36 | −7.33 | F |
| 57 | | 317.43 | −7.13 | F |

TABLE 7-continued

| | Formula V: Z=NH | | | |
|---|---|---|---|---|
| Compound Number | Structure | Mass Expected | BRD4 Binding Score | Synthetic Method |
| 58 | (structure) | 315.39 | −7.20 | F |
| 59 | (structure) | 331.46 | −7.03 | F |
| 60 | (structure) | 371.45 | −7.42 | F |

TABLE 8

| | Formula VI: Z=O | | | |
|---|---|---|---|---|
| Compound Number | Structure | Mass Expected | BRD4 Binding Score | Synthetic Method |
| 61 | (structure) | 314.36 | −7.78 | I |

TABLE 8-continued
| | Formula VI: Z=O | | | |
|---|---|---|---|---|
| Compound Number | Structure | Mass Expected | BRD4 Binding Score | Synthetic Method |
| 62 | 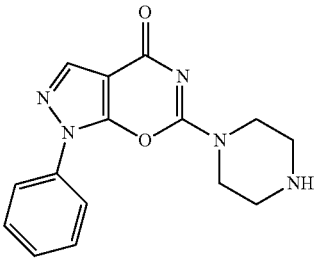 [SMILES: O=c1nc(N2CCNCC2)oc2c1cnn2-c1ccccc1] | 297.31 | −8.22 | I |
| 63 | 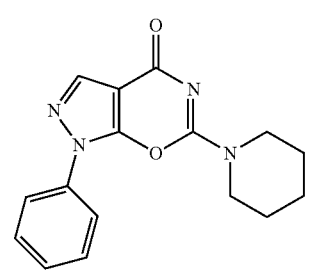 [SMILES: O=c1nc(N2CCCCC2)oc2c1cnn2-c1ccccc1] | 296.32 | −8.62 | I |
| 64 | 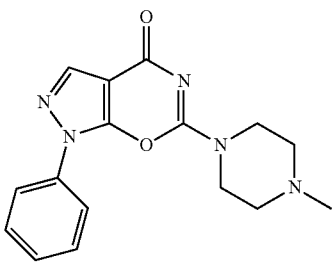 [SMILES: CN1CCN(c2nc(=O)c3cnn(-c4ccccc4)c3o2)CC1] | 311.34 | −8.34 | I |
| 65 | 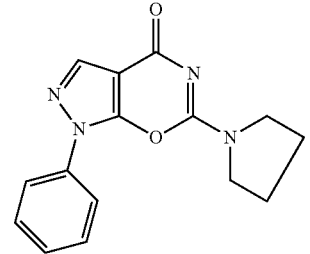 [SMILES: O=c1nc(N2CCCC2)oc2c1cnn2-c1ccccc1] | 282.30 | −8.39 | I |
| 66 | 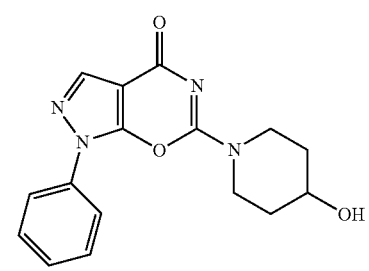 [SMILES: O=c1nc(N2CCC(O)CC2)oc2c1cnn2-c1ccccc1] | 312.32 | −8.19 | I |

TABLE 8-continued

| | Formula VI: Z=O | | | |
|---|---|---|---|---|
| Compound Number | Structure | Mass Expected | BRD4 Binding Score | Synthetic Method |
| 67 | | 310.31 | −8.75 | I |
| 68 | | 298.25 | −8.12 | I |
| 69 | | 284.27 | −7.84 | I |
| 70 | | 286.29 | −7.64 | I |
| 71 | | 302.35 | −7.26 | I |

TABLE 8-continued

Formula VI: Z=O

| Compound Number | Structure | Mass Expected | BRD4 Binding Score | Synthetic Method |
|---|---|---|---|---|
| 72 | 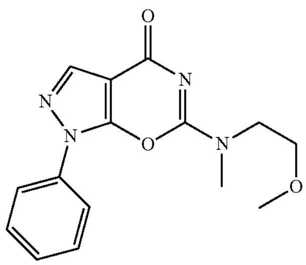 [SMILES: COCCN(C)c1nc(=O)c2cnn(-c3ccccc3)c2o1] | 300.31 | −7.48 | I |
| 73 | 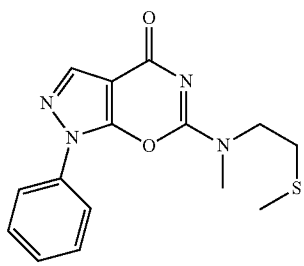 [SMILES: CSCCN(C)c1nc(=O)c2cnn(-c3ccccc3)c2o1] | 316.38 | −7.30 | I |
| 74 | 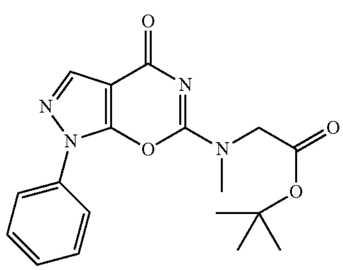 [SMILES: CN(CC(=O)OC(C)(C)C)c1nc(=O)c2cnn(-c3ccccc3)c2o1] | 356.38 | −7.56 | I |

TABLE 9

Formula VI: Z=NH

| Compound Number | Structure | Mass Expected | BRD4 Binding Score | Synthetic Method |
|---|---|---|---|---|
| 75 | 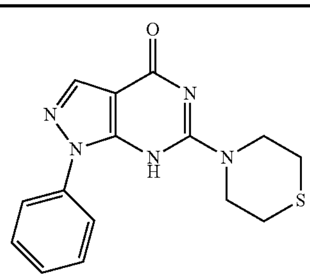 | 313.38 | −7.86 | G |

TABLE 9-continued

| | Formula VI: Z=NH | | | |
|---|---|---|---|---|
| Compound Number | Structure | Mass Expected | BRD4 Binding Score | Synthetic Method |
| 76 | | 296.33 | −8.23 | G |
| 77 | | 295.34 | −8.56 | G |
| 78 | | 310.35 | −8.36 | G |
| 79 | | 281.31 | −8.41 | G |
| 80 | | 311.34 | −8.16 | G |

TABLE 9-continued

| | Formula VI: Z=NH | | | |
|---|---|---|---|---|
| Compound Number | Structure | Mass Expected | BRD4 Binding Score | Synthetic Method |
| 81 | | 309.32 | −8.04 | G |
| 82 | | 297.27 | −8.16 | G |
| 83 | | 283.29 | −8.00 | G |
| 84 | | 285.30 | −7.68 | G |
| 85 | | 301.37 | −7.25 | G |

TABLE 9-continued

Formula VI: Z=NH

| Compound Number | Structure | Mass Expected | BRD4 Binding Score | Synthetic Method |
|---|---|---|---|---|
| 86 | 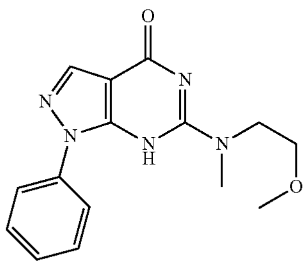 [SMILES: COCCN(C)c1nc(=O)c2cnn(-c3ccccc3)c2[nH]1] | 299.33 | −7.54 | G |
| 87 | 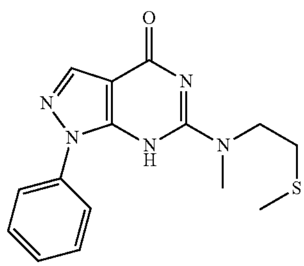 [SMILES: CSCCN(C)c1nc(=O)c2cnn(-c3ccccc3)c2[nH]1] | 315.39 | −7.28 | G |
| 88 | 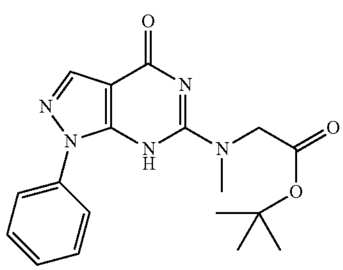 [SMILES: CN(CC(=O)OC(C)(C)C)c1nc(=O)c2cnn(-c3ccccc3)c2[nH]1] | 355.39 | −7.54 | G |

TABLE 10

Formula VII:

| Compound Number | Structure | Mass Expected | Docking Score | Synthetic Method |
|---|---|---|---|---|
| 89 | 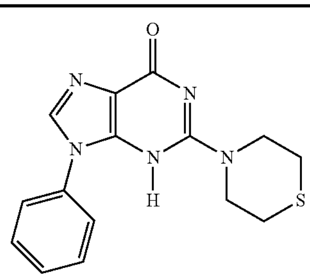 | 313.38 | −7.54 | H |

TABLE 10-continued

| Formula VII: | | | | |
|---|---|---|---|---|
| Compound Number | Structure | Mass Expected | Docking Score | Synthetic Method |
| 90 | 9-phenyl-2-(piperazin-1-yl)-purin-6(1H)-one | 296.33 | −7.78 | H |
| 91 | 9-phenyl-2-(piperidin-1-yl)-purin-6(1H)-one | 295.34 | −8.16 | H |
| 92 | 2-(4-methylpiperazin-1-yl)-9-phenyl-purin-6(1H)-one | 310.35 | −7.89 | H |
| 93 | 9-phenyl-2-(pyrrolidin-1-yl)-purin-6(1H)-one | 281.31 | −7.92 | H |
| 94 | 2-(4-hydroxypiperidin-1-yl)-9-phenyl-purin-6(1H)-one | 311.34 | −7.84 | H |

TABLE 10-continued

| | Formula VII: | | | |
|---|---|---|---|---|
| Compound Number | Structure | Mass Expected | Docking Score | Synthetic Method |
| 95 | | 309.32 | −8.04 | H |
| 96 | | 297.27 | −7.99 | H |
| 97 | | 283.29 | −7.58 | H |
| 98 | | 285.30 | −7.33 | H |
| 99 | | 301.37 | −6.81 | H |

TABLE 10-continued
Formula VII:
| Compound Number | Structure | Mass Expected | Docking Score | Synthetic Method |
|---|---|---|---|---|
| 100 | 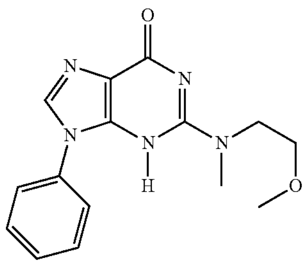 [SMILES: COCCN(C)c1nc(=O)c2ncn(-c3ccccc3)c2[nH]1] | 299.33 | −6.88 | H |
| 101 | 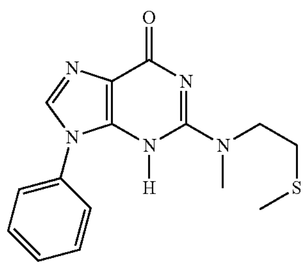 [SMILES: CSCCN(C)c1nc(=O)c2ncn(-c3ccccc3)c2[nH]1] | 315.39 | −6.75 | H |
| 102 | 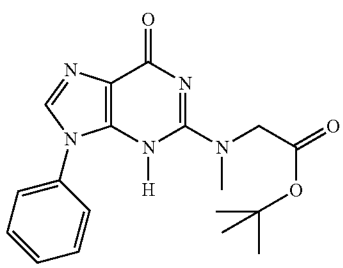 [SMILES: CN(CC(=O)OC(C)(C)C)c1nc(=O)c2ncn(-c3ccccc3)c2[nH]1] | 355.39 | −7.22 | H |
What is claimed is:
1. A compound of Formula I or a pharmaceutically acceptable salt thereof selected from the group consisting of:
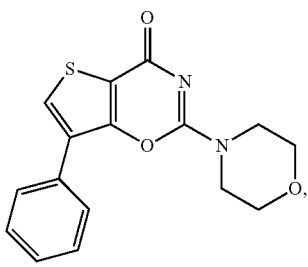
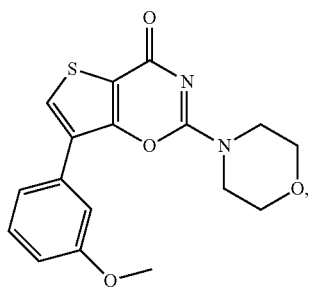
-continued
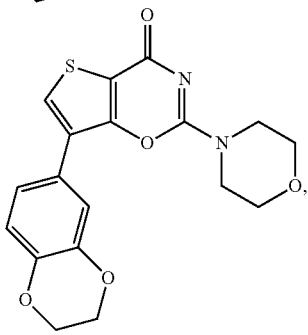
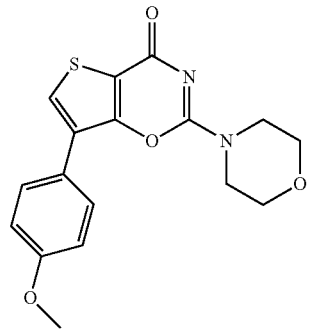

99
-continued
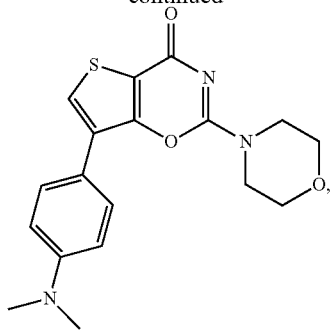
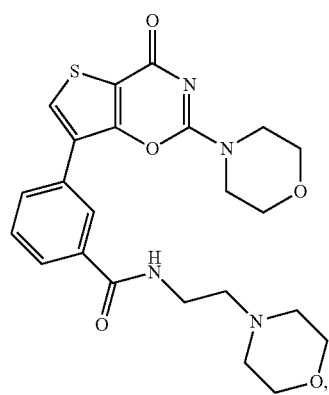
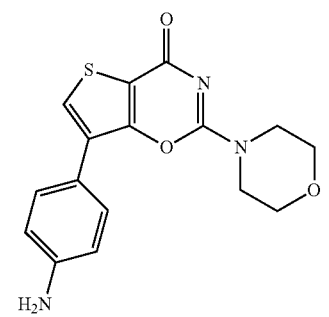
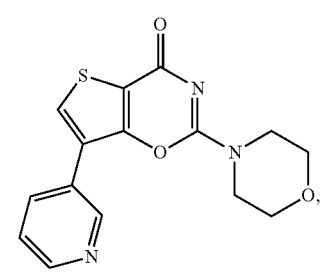
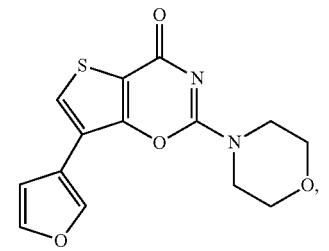
100
-continued
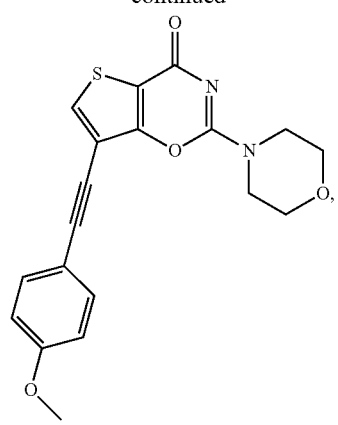
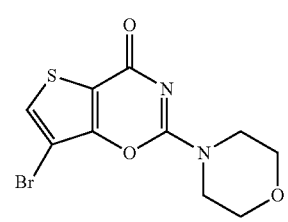
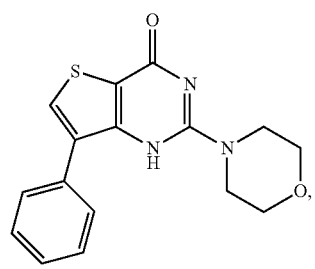
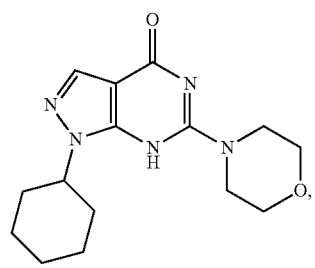
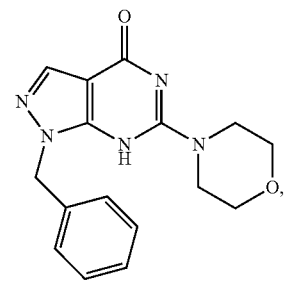
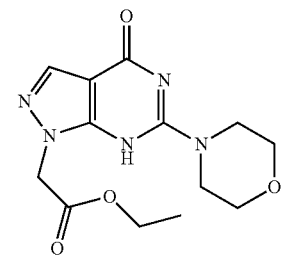

101
-continued
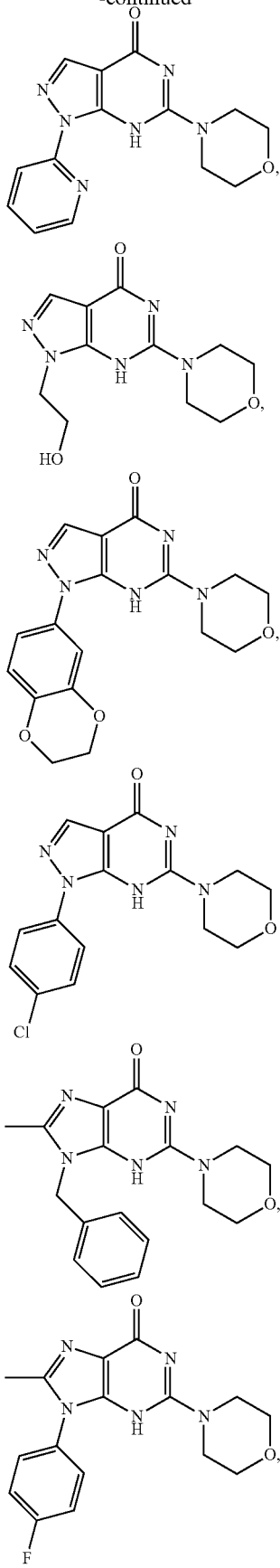
102
-continued
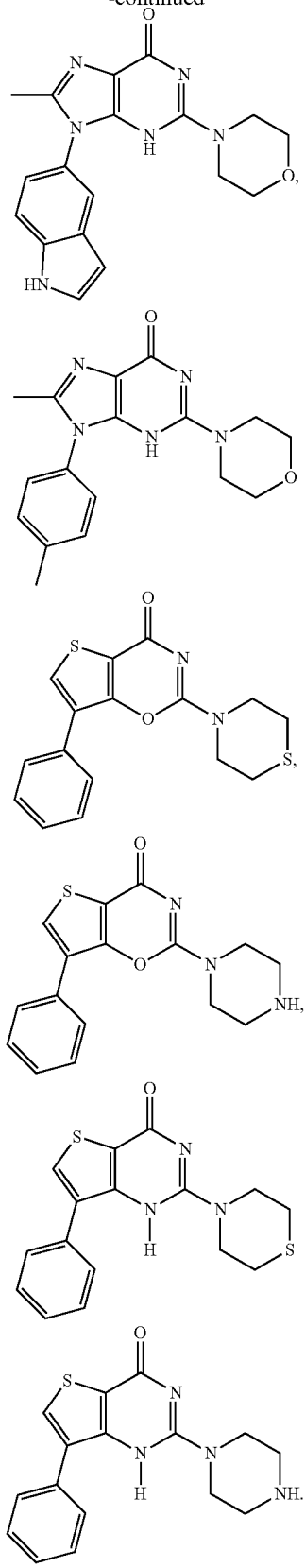
2. A compound of Formula II or V or a pharmaceutically acceptable salt thereof:

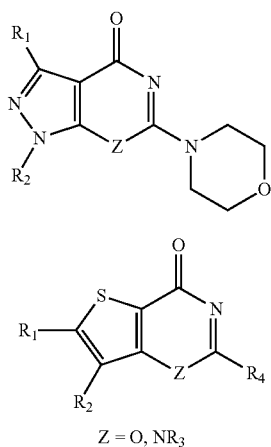

Formula III

Formula V $Z = O, NR_3$ wherein Z is O or NR3; R1, R2 and R3 are each independently selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, and substituted carbamate;

R4 is selected from:

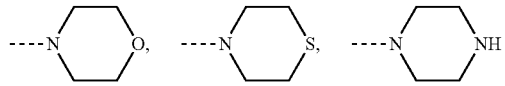

and wherein R1 excludes 3-substituted and 5-substituted pyrazoles attached at the 4 position; and
wherein R1 and R2 are not both hydrogen.

\* \* \* \* \*